US010420372B2

(12) United States Patent
Suzuki et al.

(10) Patent No.: US 10,420,372 B2
(45) Date of Patent: Sep. 24, 2019

(54) NON-BURNING TYPE FLAVOR INHALER

(71) Applicant: JAPAN TOBACCO INC., Tokyo (JP)

(72) Inventors: Akihiko Suzuki, Tokyo (JP); Kimitaka Uchii, Tokyo (JP); Takashi Hasegawa, Tokyo (JP); Manabu Yamada, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 695 days.

(21) Appl. No.: 14/689,918

(22) Filed: Apr. 17, 2015

(65) Prior Publication Data

US 2015/0237913 A1     Aug. 27, 2015

Related U.S. Application Data

(63) Continuation of application No. PCT/JP2013/077137, filed on Oct. 4, 2013.

(30) Foreign Application Priority Data

Oct. 18, 2012   (JP) ................................ 2012-231149

(51) Int. Cl.
*A24F 47/00*     (2006.01)
*A61M 15/06*     (2006.01)
*A61M 11/04*     (2006.01)

(52) U.S. Cl.
CPC .......... *A24F 47/006* (2013.01); *A24F 47/004* (2013.01); *A61M 11/04* (2013.01);
(Continued)

(58) Field of Classification Search
None
See application file for complete search history.

(56) References Cited

U.S. PATENT DOCUMENTS 4,913,168 A     4/1990   Potter et al.
5,093,894 A *   3/1992   Deevi ................ A24F 47/008
                                                     392/390

(Continued)

FOREIGN PATENT DOCUMENTS

CA    2752577 A1 *  8/2010  ........... A24F 47/002
EP    2 399 638 A1   12/2011
(Continued)

OTHER PUBLICATIONS

Extended Search Report issued in corresponding European Patent Application No. 13846670.1 dated May 25, 2016 (in English).
(Continued)

*Primary Examiner* — Michael J Felton
*Assistant Examiner* — Katherine A Will
(74) *Attorney, Agent, or Firm* — Birch, Stewart, Kolasch & Birch, LLP

(57) ABSTRACT

A non-combustion-type flavor inhaler is provided with: a heat source which has a plate-like shape having a pair of main surfaces; a flavor generation source having a plate-like shape having a pair of main surfaces; and a holder for receiving both the heat source and the flavor generation source. The heat source and the flavor generation source are stacked on each other within the holder in such a manner that one of the main surfaces of the heat source and one of the main surfaces of the flavor generation source face each other. The flavor generation source has: an introduction region for introducing air into the flavor generation source; and a delivery region for delivering air from the inside of the flavor generation source. The introduction region and the delivery region are provided on the surfaces of the flavor generation source, which are other than the main surface which faces the heat source.

13 Claims, 19 Drawing Sheets

(52) U.S. Cl.
CPC ........... *A61M 15/06* (2013.01); *A61M 11/042* (2014.02); *A61M 11/047* (2014.02)

(56) References Cited

U.S. PATENT DOCUMENTS

| | | | |
|---|---|---|---|
| 2005/0274390 A1* | 12/2005 | Banerjee | A24B 15/165 |
| | | | 131/334 |
| 2009/0162294 A1* | 6/2009 | Werner | A24F 47/006 |
| | | | 424/40 |
| 2010/0300467 A1 | 12/2010 | Kuistila et al. | |
| 2011/0290267 A1 | 12/2011 | Yamada et al. | |
| 2013/0160780 A1 | 6/2013 | Matsumoto et al. | |

FOREIGN PATENT DOCUMENTS

| | | |
|---|---|---|
| EP | 2792256 A1 | 10/2014 |
| EP | 2798968 A1 | 11/2014 |
| JP | 1-191674 A | 8/1989 |
| JP | 2011-509667 A | 3/2011 |
| WO | WO 2009/092862 A1 | 7/2009 |
| WO | WO 2010/095660 A1 | 8/2010 |
| WO | WO 2012/026481 A1 | 3/2012 |
| WO | WO 2013/111320 A1 | 8/2013 |
| WO | WO 2013/111792 A1 | 8/2013 |

OTHER PUBLICATIONS

International Search Report, issued in PCT/JP2013/077137, dated Jan. 7, 2013.

* cited by examiner

NON-BURNING TYPE FLAVOR INHALER

TECHNICAL FIELD

The present invention relates to a non-burning type flavor inhaler that enables inhaling of flavors without burning.

BACKGROUND ART

In recent years, in order to control the occurrence of smoke, a non-burning type flavor inhaler (for example, a smokeless tobacco) that enables inhaling of flavors without burning has been provided (for example, Patent Literature 1). Specifically, the non-burning type flavor inhaler includes a heat source having a cylindrical shape, and a flavor generating source that has a columnar shape and that is provided on the inner side of the heat source. Alternatively, the non-burning type flavor inhaler includes a heat source having a columnar shape, and a flavor generating source that has a cylindrical shape and that is provided on the outer side of the heat source.

However, in the above-described non-burning type flavor inhaler, it is necessary to process the heat source or the flavor generating source in a cylindrical shape, and the manufacture of the heat source or the flavor generating source is complicated. Furthermore, in a case of the above-described cylindrical non-burning type flavor inhaler, in order to realize a sufficient heat generation continuity, the heat source is required to have a predetermined volume, and on the other hand, in order to realize a sufficient supply of the flavor, the flavor generating source is required to have a predetermined volume, which makes it difficult to realize a flavor inhaler that is thin and has excellent portability and handling.

CITATION LIST

Patent Literature

[Patent Literature 1] Japanese Patent Application Publication No. 2011-509667

SUMMARY OF INVENTION

The present invention is summarized as a non-burning type flavor inhaler, comprising: a heat source having a plate shape including a pair of main surfaces; a flavor generating source having a plate shape including a pair of main surfaces; and a holder that stores the heat source and the flavor generating source, wherein the heat source and the flavor generating source are laminated inside the holder so that one of the main surfaces provided in the heat source and one of the main surfaces provided in the flavor generating source are facing each other, the flavor generating source has an inlet portion through which air is led into the flavor generating source, and an outlet portion from which air is led out from the flavor generating source, and the inlet portion and the outlet portion are provided on surfaces other than the main surface facing the heat source, among the surfaces provided in the flavor generating source.

DESCRIPTION OF EMBODIMENTS

First Embodiment (1) Configuration of Non-Burning Type Flavor Inhaler

Figure 1:
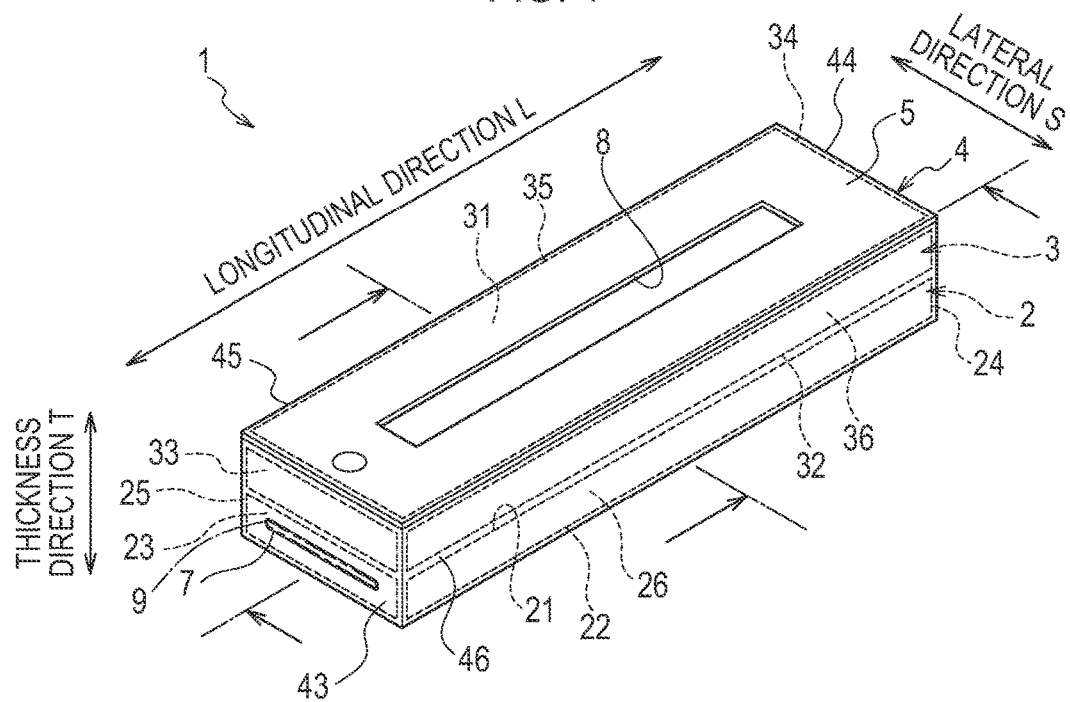
FIG. 1 is a perspective view of a non-burning type flavor inhaler 1 according to a first embodiment.
Figure 2:
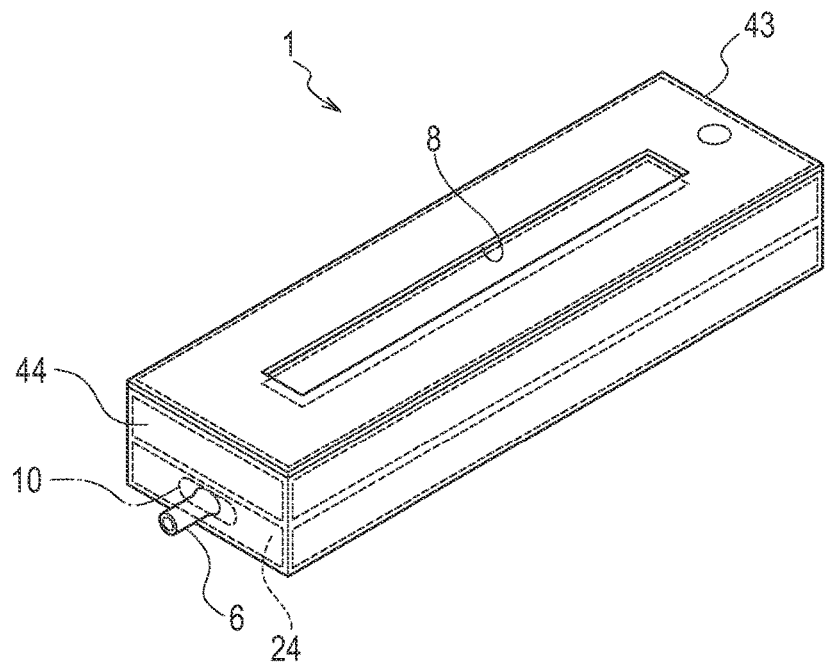
FIG. 2 is a perspective view of the non-burning type flavor inhaler 1 according to the first embodiment.
Figure 3:
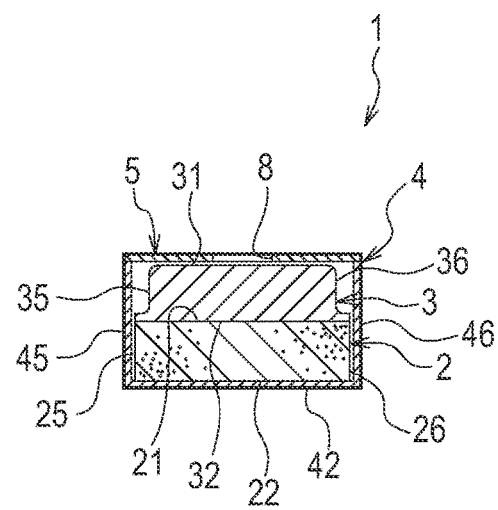
FIG. 3 is a cross-sectional view along a lateral direction of the non-burning type flavor inhaler 1 according to the first embodiment.
Figure 4:
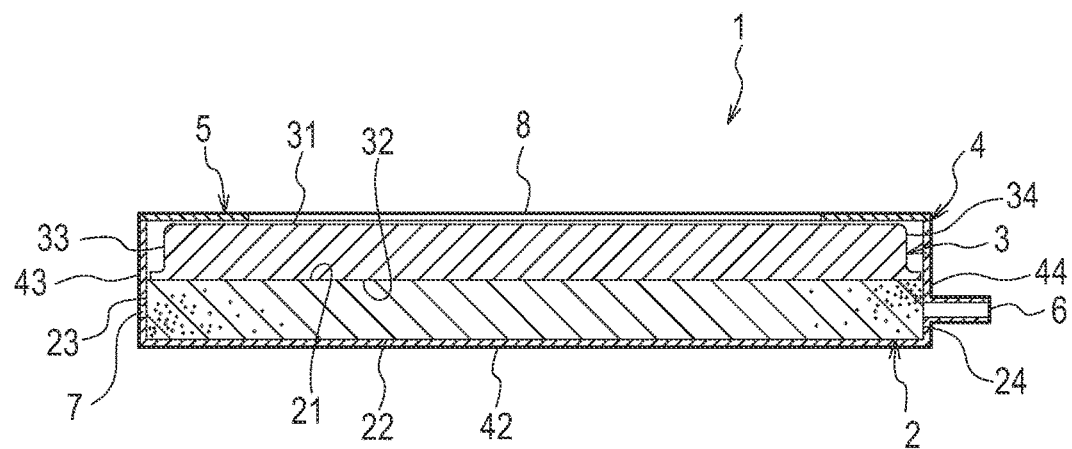
FIG. 4 is a cross-sectional view along a longitudinal direction of the non-burning type flavor inhaler 1 according to the first embodiment.

The configuration of a non-burning type flavor inhaler 1 according to a first embodiment of the present invention is described below on the basis of FIG. 1 through FIG. 4. FIG. 1 and FIG. 2 are perspective views of the non-burning type flavor inhaler 1 according to the first embodiment. FIG. 3 is a cross-sectional view along a lateral direction of the non-burning type flavor inhaler 1 according to the first embodiment. FIG. 4 is a cross-sectional view along a longitudinal direction of the non-burning type flavor inhaler 1 according to the first embodiment.

As shown in FIG. 1 and FIG. 2, the non-burning type flavor inhaler 1 includes a flavor generating source 2, a heat source 3, a holder 4, a lid 5, and a mouthpiece 6. The flavor generating source 2 and the heat source 3 are laminated inside the holder 4, and are contained inside the holder 4. The non-burning type flavor inhaler 1 has an approximately rectangular parallelepiped shape including a longitudinal direction L, a lateral direction S, and a thickness direction T. The longitudinal direction L, for example, is a direction in which the air passing through the flavor generating source 2 flows. The lateral direction S is a direction approximately orthogonal to the longitudinal direction L and the thickness direction T. The thickness direction T is a direction in which the flavor generating source 2 and the heat source 3 are laminated.

Here, the size of the non-burning type flavor inhaler 1 in the lateral direction S is smaller than the size of the non-burning type flavor inhaler 1 in the longitudinal direction L. Furthermore, the size of the non-burning type flavor inhaler 1 in the thickness direction T is smaller than the size of the non-burning type flavor inhaler 1 in the lateral direction S.

As shown in FIG. 1 and FIG. 2, the flavor generating source 2 has the widest area and a plate shape (an approximately rectangular parallelepiped shape) including a pair of main surfaces 21 and 22 defined by the longitudinal direction L and the lateral direction S, a pair of side surfaces 23 and 24 defined by the lateral direction S and the thickness direction T, and a pair of side surfaces 25 and 26 defined by the longitudinal direction L and the thickness direction T. The pair of main surfaces 21 and 22 defined by the lateral direction S and the longitudinal direction L orthogonal to each other have a rectangular shape.

The flavor generating source 2 may be realized by shredding a plant material such as tobacco leaves into an optional size and then filling the shredded leaves. Furthermore, the flavor generating source 2 may be realized by forming a plant material such as tobacco leaves in the shape of a sheet and then laminating the sheets, or the flavor generating source 2 may be a granular material wrapped in a pouch made of a nonwoven cloth having air permeability. Moreover, the flavor generating source 2 may be a compact manufactured by a method such as tablet making, extrusion, injection molding, and the like. In addition, as the plant material such as tobacco leaves, a plant material on which a process well-known in the art, such as heating and drying, is performed, if necessary, may be used.

As shown in FIG. 1 and FIG. 2, the flavor generating source 2 is a compact having air permeability. In the first embodiment, the flavor generating source 2 has air permeability that enables air to flow through the inside of the flavor generating source 2 along the longitudinal direction L. For example, the flavor generating source 2 is realized by sandwiching a mixture of a granular tobacco body and a binding agent such as a thermoplastic resin between nonwoven cloths, whereby the flavor generating source 2 is formed in a sheet shape through thermal fusion bonding.

As shown in FIG. 1, the side surface 23 of the flavor generating source 2 has an inlet portion 9 for leading in air. The inlet portion 9 is a portion exposed to an inlet opening 7 of the holder 4 described later.

As shown in FIG. 2, the side surface 24 of the flavor generating source 2 has an outlet portion 10 for leading out air. The outlet portion 10 is a portion exposed to a mouthpiece 6 described later. The inlet portion 9 and the outlet portion 10 will be described in detail later.

The flavor generating source 2 has air permeability. That is, the main surfaces 21 and 22, the pair of side surfaces 23 and 24, and the pair of side surfaces 25 and 26 of the flavor generating source 2 have air permeability. For example, the air led in from the inlet portion 9 of the flavor generating source 2 passes through the inside of the flavor generating source 2, and is led out from the outlet portion 10. A flavor is added to the air led in from the inlet portion 9 while the flavor passes through the flavor generating source 2. A flavor capable of relaxing a user is preferably included as the flavor added to the air. The tobacco flavor is known as a flavor capable of relaxing a user. For example, the flavor generating source preferably has a tobacco powder for adding the tobacco flavor.

Here, the grain size of the tobacco powder is preferably from 0.1 mm to 2.0 mm. The filler content of the tobacco powder is preferably from 100 mg to 1000 mg. In addition to the tobacco powder, the flavor generating source 2 may include a flavor stabilizer, such as menthol essence, propylene glycol, or a medium chain triglyceride (MCT), and various types of essences and flavor compounds that are well-known in the art may also be added.

When the flavor generating source 2 having tobacco powder is formed as a sheet-shaped compact having air permeability, it is preferable to sandwich a mixture of the tobacco powder and a binder such as a thermoplastic resin by a nonwoven cloth from the top and bottom, and form the flavor generating source 2 in a sheet shape through thermal fusion bonding. If the total of the tobacco powder and the thermoplastic resin is assumed to be 100 wt % (weight percent), it is preferable to blend the binder of the thermoplastic resin in a range of 10 to 70 wt % (weight percent), and preferably in the range of 20 to 50 wt % with respect to the tobacco powder.

It is preferable to use a polyvinyl alcohol, such as polyethylene and polyamide, etc., or a polyurethane resin as the thermoplastic resin. It is further preferable to use an ethylene vinylalcohol copolymer (EVA).

As shown in FIG. 1 and FIG. 2, the heat source 3 is formed in a plate shape configured by a pair of main surfaces 31 and 32 having the widest area, a pair of side surfaces 33 and 34 along the lateral direction, and a pair of side surfaces 35 and 36 along the longitudinal direction L.

In order to heat the flavor generating source 2, the heat source 3 generates a heat of 60° C. or more. Particularly, it is preferable that the heat source 3 generates a heat of 90° C. or more. It is possible to adopt electric heat and various types of heat of chemical reactions as the mode of generation of heat by the heat source 3. Chemical reactions that make use of the oxidation reaction heat using the oxygen in the atmosphere, as well as the latent heat are well-known as the chemical reactions accompanying the generation of heat. In the first embodiment, it is preferable to use the oxidation reaction heat of iron powder as the oxidation reaction heat. More particularly, the heat source 3 is configured by iron powder and an outer bag that stores the iron powder. The outer bag, for example, is configured by a nonwoven cloth having apertures that are smaller than the grain size of the iron powder.

In such cases, it is preferable to secure air permeability of the heat source 3 in a state when the heat source 3 is stored in the holder 4. As described later, in the first embodiment, since the lid 5 has an opening 8, the air is supplied from the opening 8 to the main surface 31 of the heat source 3. On the other hand, the main surface 32 of the heat source 3 facing the flavor generating source 2 is preferably configured by a member that does not have air permeability. Alternatively, a member that does not have air permeability may be pasted on the main surface 32 of the heat source 3.

If the oxidation reaction heat of iron powder is used as the oxidation reaction heat, the heat source 3 preferably includes iron powder, activated carbon, water, and sodium chloride as the heating element. If the total of the iron powder, activated carbon, water, and sodium chloride in the heating element is assumed to be 100 wt % (weight percent), the iron powder is preferably selected in the range of 30 to 60 wt % (weight percent). Similarly, the activated carbon is preferably selected in the range of 10 to 50 wt % (weight percent). Similarly, water is preferably selected in the range of 10 to 30 wt % (weight percent). Moreover, sodium chloride is preferably selected in the range of 0.5 to 7 wt % (weight percent).

For example, when activated carbon having a specific surface area of 1700 m²/g is used, the weight percent of the iron powder, activated carbon, water, and sodium chloride is preferably 46:30:20:4 with the total of the iron powder, activated carbon, water, and sodium chloride being 100 wt % (weight percent). The total weight of the iron powder, activated carbon, water, and sodium chloride in the heat source 3 is preferably from 0.5 to 1.5 g.

If the flavor generating source 2 includes tobacco powder, the temperature of the heat generated from the heat source 3 is preferably 90° C. or more. If the temperature of the heat generated from the heat source 3 is 90° C. or more, the flavor generating source 2 is heated sufficiently, and as a result, it is possible for a user to inhale sufficient flavor from the tobacco powder.

As shown in FIG. 1 and FIG. 2, the holder 4 has a box shape for storing the flavor generating source 2 and the heat source 3. Specifically, the holder 4 has a plate-shaped bottom panel 42, a pair of plate-shaped wall panels 43 and 44 that rise up from near the lateral direction S of the bottom panel 42, and a pair of plate-shaped wall panels 45 and 46 that rise up from near the longitudinal direction L of the bottom panel 42.

As shown in FIG. 1, the wall panel 43 of the holder 4 has an inlet opening 7 for leading in air. For example, the inlet opening 7 is an opening having a line shape. The inlet opening 7 may be configured by a plurality of dot-shaped openings.

As shown in FIG. 2, a mouthpiece 6 is provided on the wall panel 44 of the holder 4 for the user to inhale the flavor.

As shown in FIG. 1 and FIG. 2, the lid 5 is formed on the opposite side of the bottom panel 42 of the holder 4. The lid 5 functions as a lid of the holder 4 and has an opening 8. The opening 8 is formed to enable securing sufficient contact area between the heat source 3 and the air.

The mouthpiece 6 leads to the inner side of the holder 4, and has a cylindrical shape. The mouthpiece 6 is formed in the center of the wall panel 44 in the lateral direction S.

As shown in FIG. 3 and FIG. 4, the holder 4 has a holding structure for holding the flavor generating source 2 and the heat source 3. As shown in FIG. 3, the flavor generating source 2 and the heat source 3 are laminated inside the holder 4 so that the main surface 32 of the heat source 3 and the main surface 21 of the flavor generating source 2 are facing each other. The main surface 31 of the heat source 3 and the lid 5 lie in proximity, and are stored in the holder 4 so that the air is supplied from the main surface 31 of the heat source 3 via the opening 8 of the lid 5. The flavor generating source is stored in the holder 4 so that the main surface 22 of the flavor generating source 2 and the bottom panel 42 of the holder 4 are in contact. That is, the thickness obtained by laminating the flavor generating source 2 and the heat source 3, in the thickness direction T, is almost same as the thickness of the holder 4. Furthermore, the side surface 25 of the flavor generating source 2 and the side surface 35 of the heat source 3, as well as the wall panel 45 of the holder 4 lie in proximity. The side surface 26 of the flavor generating source 2 and the side surface 36 of the heat source 3, as well as the wall panel 46 of the holder 4 lie in proximity. That is, the width of the flavor generating source 2 and the heat source 3 in the lateral direction S, and the width of the holder 4 are almost the same.

As shown in FIG. 4, the flavor generating source 2 is stored in the holder 4 so that the side surface 23 of the flavor generating source 2 and the inlet opening 7 are facing each other, and the side surface 24 of the flavor generating source 2 and the mouthpiece 6 are facing each other. Furthermore, the side surface 23 of the flavor generating source 2 and the side surface 33 of the heat source 3, as well as the wall panel 43 of the holder 4 lie in proximity. The side surface 24 of the flavor generating source 2 and the side surface 34 of the heat source 3, as well as the wall panel 44 of the holder 4 lie in proximity. That is, the length of the flavor generating source 2 and the heat source 3 in the longitudinal direction L, and the length of the holder 4 are almost the same.

(2) Inlet Portion and Outlet Portion

Figure 5:
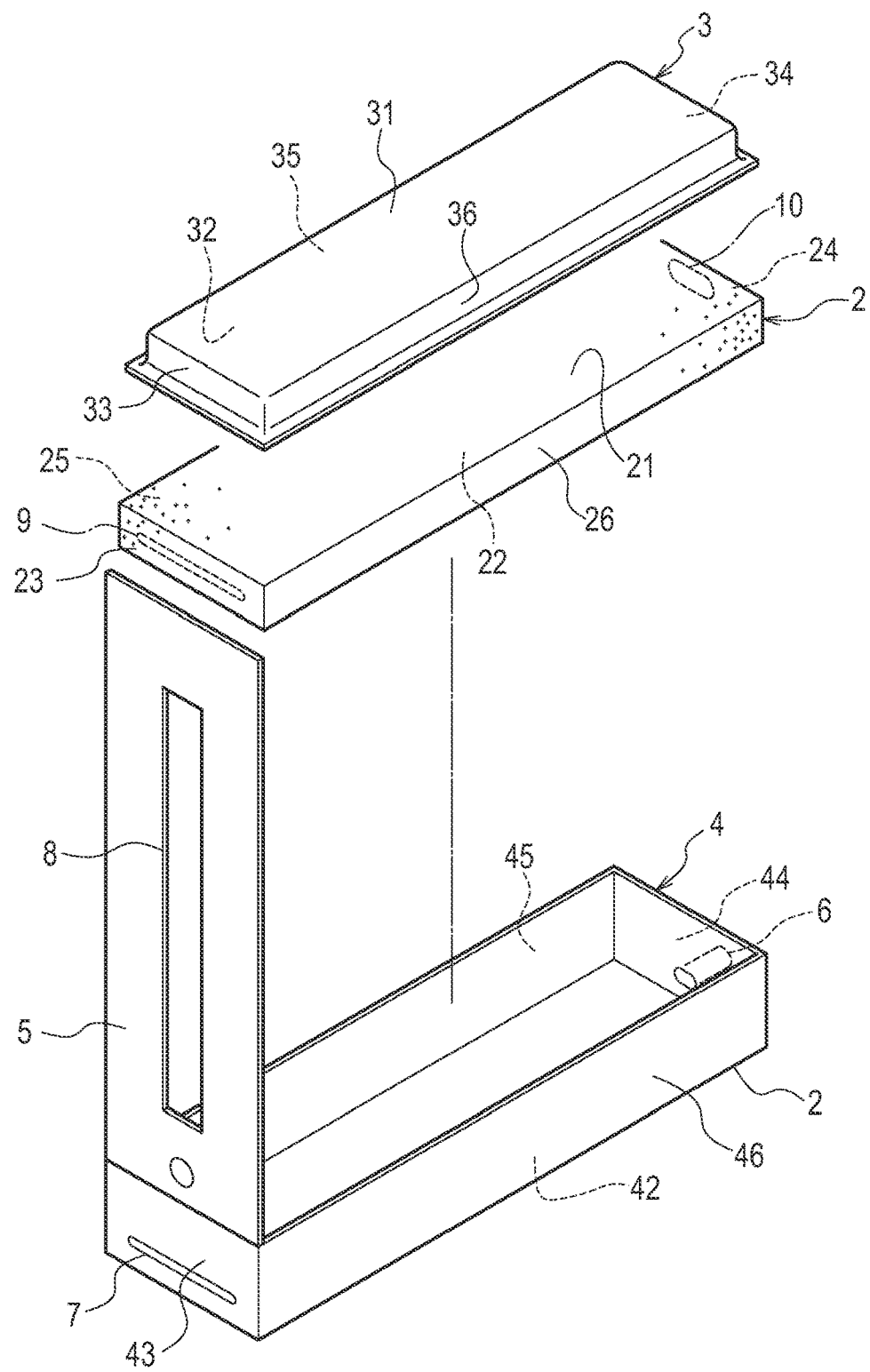
FIG. 5 is a perspective view of the non-burning type flavor inhaler 1 having an open lid 5 according to the first embodiment.

Next, the inlet portion 9 and the outlet portion 10 of the flavor generating source 2 will be described on the basis of FIG. 5. FIG. 5 is a perspective view of the non-burning type flavor inhaler 1 having the open lid 5 according to the first embodiment.

The inlet portion 9 is the portion where the air flowing in from the inlet opening 7 of the holder 4 is led in to the flavor generating source 2, and this area faces the inlet opening 7 of the holder 4. The outlet portion 10 is the portion where the air that has passed through the inside of the flavor generating source 2 is led out, and in the first embodiment, the outlet portion 10 faces the mouthpiece 6 of the holder 4, as shown in FIG. 5. That is, the inlet portion 9 and the outlet portion 10 are provided on the surfaces other than the main surfaces 21 and 22 facing the heat source 3, among the surfaces provided in the flavor generating source 2.

(3) Flow Path of Air in the Non-Burning Type Flavor Inhaler

Figure 6:
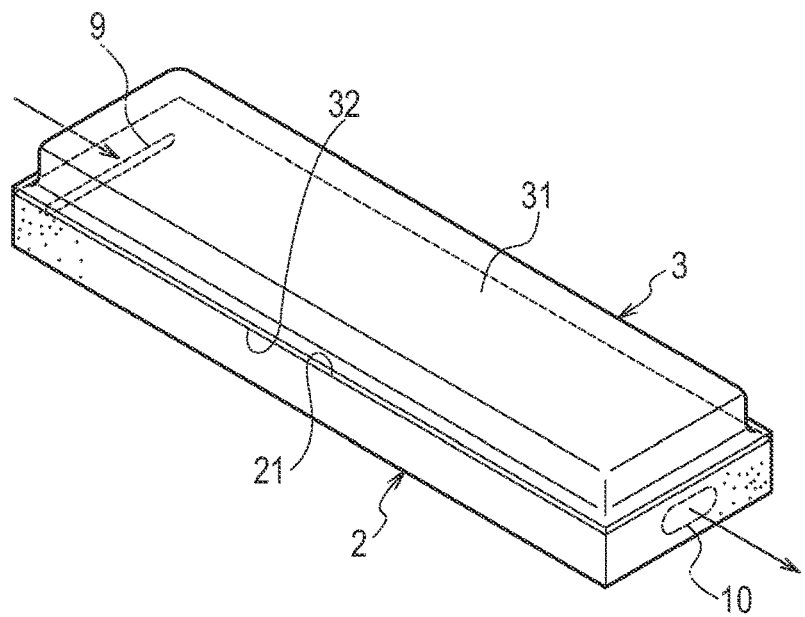
FIG. 6 is a drawing showing a flow path of air in a case when a flavor generating source 2 and a heat source 3 are inserted in the non-burning type flavor inhaler 1 according to the first embodiment.

Next, the flow path of air in the non-burning type flavor inhaler 1 will be described on the basis of FIG. 6. FIG. 6 is a drawing showing a flow path of air in the flavor generating source 2 and the heat source 3, in a case when the flavor generating source 2 and the heat source 3 are inserted in the holder 4 of the non-burning type flavor inhaler 1 according to the first embodiment.

As shown in FIG. 6, the flavor generating source 2 and the heat source 3 are laminated and stored inside the holder 4 so that one main surface 32 of the heat source 3 and one main surface 21 of the flavor generating source 2 are facing each other, and the entire surface of the main surface 21 of the flavor generating source 2 is heated via the entire surface of the main surface 32 of the heat source 3. At this time, upon being inhaled by the user, the air led in from the inlet portion 9 of the flavor generating source 2 via the inlet opening 7 of the holder 4 passes through the inside of the flavor generating source 2, and is led out from the outlet portion 10 of the flavor generating source 2 without changing the direction. Since the main surface 32 of the heat source 3 does not have air permeability, the air led in from the inlet portion 9 of the flavor generating source 2 is led out from the outlet portion 10 of the flavor generating source 2 without passing through the inside of the heat source 3. That is, the holder 4 has a flow path through which the air led out from the outlet portion 10 is led to the mouthpiece 6. Specifically, the flow path is formed along the longitudinal direction L in the pair of main surfaces 21 and 22 provided in the flavor generating source 2 so that the air pass through the inside of the flavor generating source 2. The air led in from the inlet portion 9 of the flavor generating source 2 via the inlet opening 7 of the holder 4 passes through the outlet portion 10 of the flavor generating source 2, and is led out straight from the mouthpiece 6.

(4) Effect

According to the non-burning type flavor inhaler 1 of the first embodiment, since the flavor generating source 2 and the heat source 3 are in the shape of a plate, as compared to a case in which the flavor generating source 2 and the heat source 3 are processed in a columnar shape or a cylindrical shape, it is possible to easily process the flavor generating source 2 and the heat source 3. If the flavor generating source 2 or the heat source 3 has a shape of granular manner, then as compared to a case in which the flavor generating source 2 and the heat source 3 are processed in a cylindrical shape, particularly, it is possible to easily process the flavor generating source 2 and the heat source 3.

According to the non-burning type flavor inhaler 1 of the first embodiment, since the entire surface of the main surface 21 of the flavor generating source 2 is heated via the entire surface of the main surface 32 of the heat source 3, it is possible to sufficiently heat the flavor generating source 2. It is possible to sufficiently heat the flavor generating source 2, and thus, upon inhalation by the user, it is possible to add a sufficient flavor to the air passing through the flavor generating source 2.

According to the non-burning type flavor inhaler 1 of the first embodiment, upon inhalation by the user, the air passes across the entire inside of the flavor generating source 2, because of which it is possible to add a sufficient flavor to the air passing through the flavor generating source 2.

According to the non-burning type flavor inhaler 1 of the first embodiment, since the air led in from the inlet portion 9 of the flavor generating source 2 passes only through the inside of the flavor generating source 2 without passing through the inside of the heat source 3, upon inhalation by the user, it is possible to control the rise in the air-flow resistance.

According to the non-burning type flavor inhaler 1 of the first embodiment, the size of the non-burning type flavor inhaler 1 in the thickness direction T is smaller than the size of the non-burning type flavor inhaler 1 in the lateral direction S. Therefore, as compared to a case in which the non-burning type flavor inhaler has a columnar shape, it is possible to reduce the non-burning type flavor inhaler 1 in size even if the volume of the non-burning type flavor inhaler is the same.

(5) Configuration of the Non-Burning Type Flavor Inhaler According to a First Modification Hereinafter, a first modification of the first embodiment will be described. Mainly, the differences from the first embodiment are explained below. The same symbols have been used for the configuration the same as the first embodiment, and the explanation has been omitted.

In the first embodiment, the heat source is laminated on one of the pair of main surfaces of the flavor generating source 2. In contrast, in the first modification, the heat sources are laminated on both of the pair of main surfaces of the flavor generating source 2.

Figure 7:
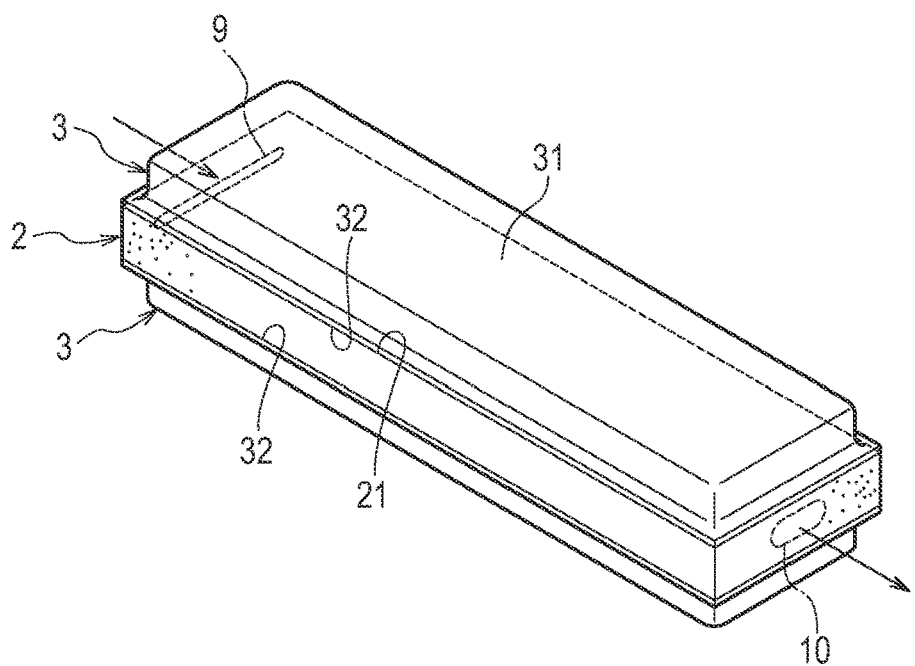
FIG. 7 is a drawing showing a flow path of air in a case when the flavor generating source 2 and two heat sources 3 are inserted in the non-burning type flavor inhaler 1 according to a modification 1 of the first embodiment.

FIG. 7 is a drawing showing a flow path of air in the flavor generating source 2 and the heat source 3, in a case when the flavor generating source 2 and two heat sources 3 are inserted in the holder 4 of the non-burning type flavor inhaler 1 according to the first modification.

As shown in FIG. 7, the flavor generating source 2 and the heat source 3 are laminated inside the holder 4 so that one main surface 32 of the heat source 3 and one main surface 21 of the flavor generating source 2 are facing each other, and one main surface 32 of the other heat source 3 and the other main surface 22 of the flavor generating source 2 are facing each other. Therefore, the entire surface of the main surfaces 21 and 22 of the flavor generating source 2 is heated via the entire surface of the main surface 32 of the heat sources 3. In such a case, upon being inhaled by the user, the air led in from the inlet portion 9 of the flavor generating source 2 via the inlet opening 7 of the holder 4 passes through the inside of the flavor generating source 2, and then passes through the outlet portion 10 of the flavor generating source 2 before being led out from the mouthpiece 6 without changing the direction. Since a member that does not have air permeability is pasted on the main surface 32 of the heat source 3 and the main surface 32 of the other heat source 3, the air led in from the inlet portion 9 of the flavor generating source 2 is led out from the outlet portion 10 of the flavor generating source 2 without passing through the inside of the heat source 3 and the other heat source 3. That is, the holder 4 that stores the flavor generating source 2 and the heat sources has a flow path in the longitudinal direction L through which air flows.

According to the non-burning type flavor inhaler 1 of the first modification, since both of the pair of main surfaces 21 and 22 of the flavor generating source 2 are heated via the main surface 32 of the two heat sources 3, it is possible to sufficiently heat the flavor generating source 2. It is possible to sufficiently heat the flavor generating source 2, and thus, upon inhalation by the user, it is possible to add a sufficient flavor to the air passing through the flavor generating source 2.

Second Embodiment

Hereinafter, a second embodiment will be described. Mainly, the differences from the first embodiment are explained below. The same symbols have been used for the configuration the same as the first embodiment, and the explanation has been omitted.

(1) Configuration of Non-Burning Type Flavor Inhaler

In the first embodiment, since the inlet opening is formed in a wall panel rising up from near the lateral direction of the bottom panel of the holder, the inlet portion of air into the flavor generating source is provided on the side surface of the flavor generating source facing the inlet opening.

Figure 8:
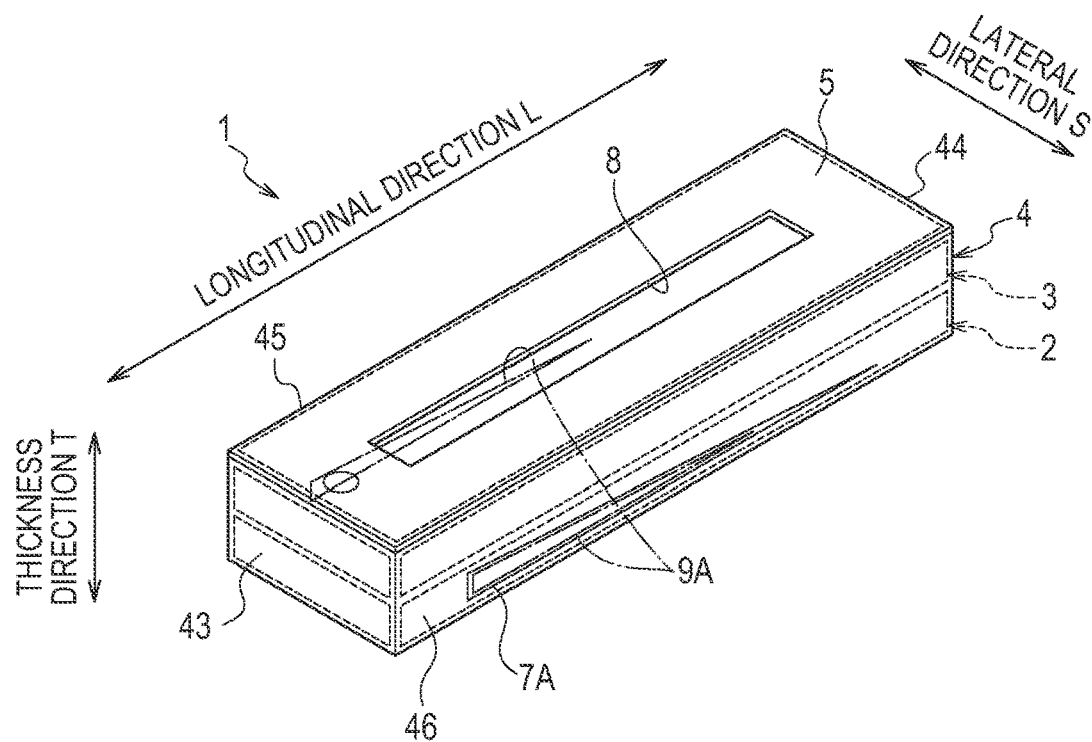
FIG. 8 is a perspective view of the non-burning type flavor inhaler 1 according to a second embodiment.
Figure 9:
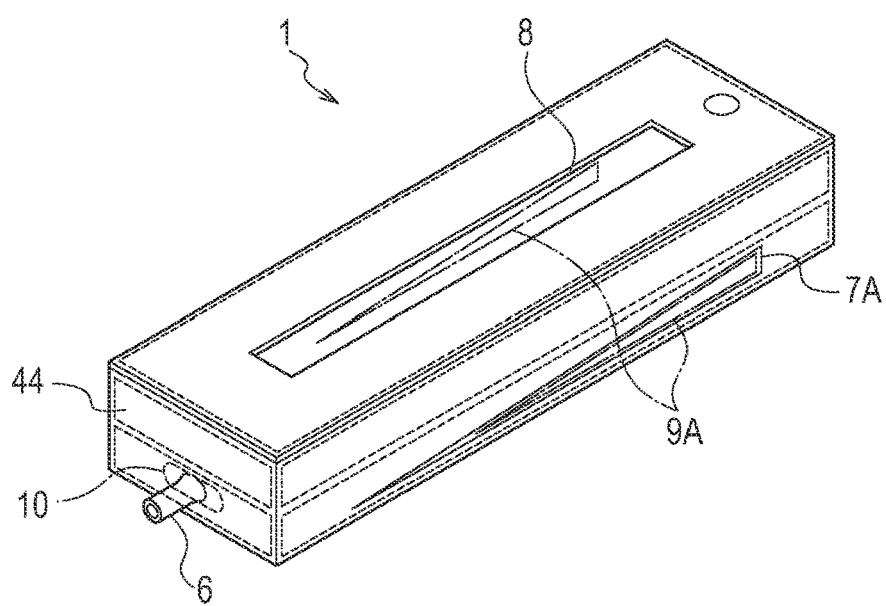
FIG. 9 is a perspective view of the non-burning type flavor inhaler 1 according to the second embodiment.

In contrast, in the second embodiment, the inlet openings are formed in both the wall panels rising up from near the longitudinal direction of the bottom panel of the holder, and the inlet portions of air into the flavor generating source are provided on both the side surfaces of the flavor generating source facing the inlet opening. FIG. 8 and FIG. 9 are perspective views of the non-burning type flavor inhaler 1 according to the second embodiment.

As shown in FIG. 8 and FIG. 9, the inlet opening 7A is an opening that leads in air, and is formed on both the wall panels 45 and 46 of the holder 4. The inlet opening 7A is formed so that the area of the inlet opening 7A reduces gradually from the wall panel 43 along the lateral direction toward the wall panel 44 along the lateral direction. That is, the inlet opening 7A is formed so that the area of the inlet opening 7A reduces gradually from the wall panel 43 that does not have the mouthpiece 6 toward the wall panel 44 that has the mouthpiece 6. That is, the inlet opening 7A, for example, is preferably formed in the shape of an isosceles triangle.

(2) Inlet Portion and Outlet Portion

Figure 10:
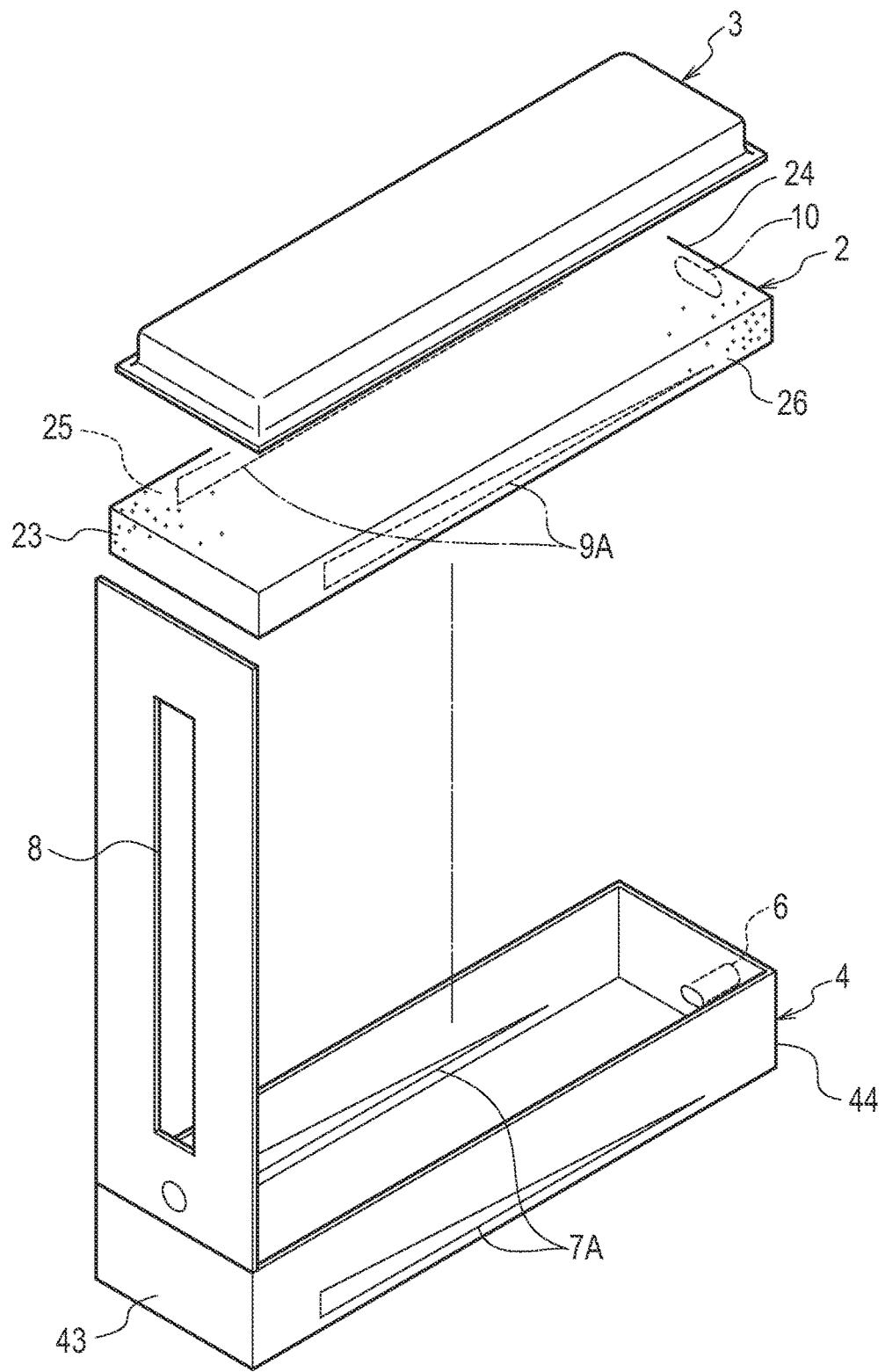
FIG. 10 is a perspective view of the non-burning type flavor inhaler 1 having the open lid 5 according to the second embodiment.

Next, the inlet portion 9A and the outlet portion 10 of the flavor generating source 2 will be described on the basis of FIG. 10. FIG. 10 is a perspective view of the non-burning type flavor inhaler 1 having the open lid 5 according to the second embodiment.

The inlet portion 9A is the portion where the air flowing in from the inlet opening 7A of the holder 4 is led in to the flavor generating source 2, and this area faces the inlet opening 7A provided on both side walls of the holder 4. The outlet portion 10 is the portion where the air that has passed through the inside of the flavor generating source 2 is led out, and in the second embodiment, the outlet portion 10 faces the mouthpiece 6 of the holder 4, as shown in FIG. 10. That is, the inlet portion 9A and the outlet portion 10 are provided on the surfaces other than the main surfaces 21 and 22 facing the heat source 3, among the surfaces provided in the flavor generating source 2.

As shown in FIG. 10, the inlet portion 9A of the flavor generating source 2 faces each inlet opening 7A of the holder 4. To enable approximately the same amount of air to be led in throughout the longitudinal direction L in the inlet portion 9A of the flavor generating source 2, the inlet opening 7A of the holder 4 is formed so that the area of the inlet opening 7A reduces gradually from the wall panel 43 that does not have the mouthpiece 6 toward the wall panel 44 that has the mouthpiece 6.

(3) Flow Path of Air in the Non-Burning Type Flavor Inhaler

Figure 11:
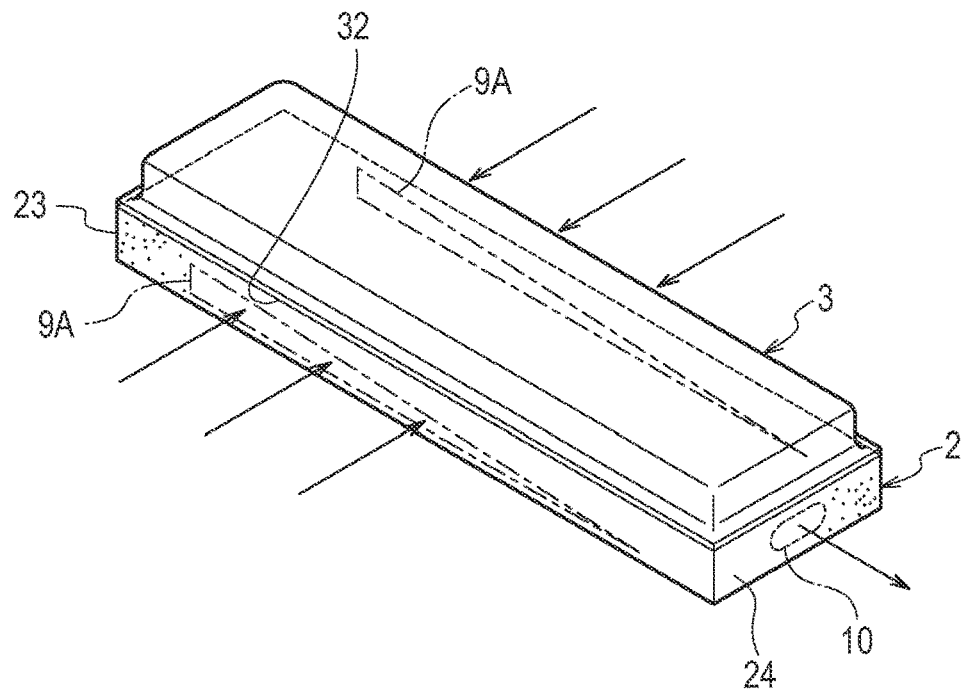
FIG. 11 is a drawing showing a flow path of air in a case when the flavor generating source 2 and the heat source 3 are inserted in the non-burning type flavor inhaler 1 according to the second embodiment.

Next, the flow path of air in the non-burning type flavor inhaler 1 will be described on the basis of FIG. 11. FIG. 11 is a drawing showing a flow path of air in the flavor generating source 2 and the heat source 3, in a case when the flavor generating source 2 and the heat source 3 are inserted in the holder 4 of the non-burning type flavor inhaler 1.

As shown in FIG. 11, upon being inhaled by the user, the air led in from both the inlet portions 9A of the flavor generating source 2 via both the inlet opening 7A of the holder 4 passes through the outlet portion 10 of the flavor generating source 2 after changing the direction inside the flavor generating source 2, and is then led out from the mouthpiece 6. As the area of the inlet opening 7A keeps widening further away from the mouthpiece 6, approximately the same amount of air is led into the flavor generating source 2 in the inlet portion 9A close to the side surface 23 and the inlet portion 9A close to the side surface 24.

Since the main surface 32 of the heat source 3 facing the main surface 21 of the flavor generating source 2 does not have air permeability, the air led in from the inlet portion 9A of the flavor generating source 2 is led out from the outlet portion 10 of the flavor generating source 2 without passing through the inside of the heat source 3. That is, the air led in to the inlet portion 9A parallel to the lateral direction S is led out from the outlet portion 10 after changing the direction in the flavor generating source 2 so as to be parallel to the longitudinal direction L. That is, the holder 4 that stores the flavor generating source 2 and the heat source 3 according to the second embodiment has a flow path in which the air led in along the lateral direction S is led out from the mouthpiece after changing the direction so as to become parallel to the longitudinal direction L.

(4) Effect

According to the non-burning type flavor inhaler 1 of the second embodiment, since the air is led in from the inlet portion 9A provided in the pair of side surfaces 25 and 26, and the air passes across the entire inside of the flavor generating source 2, upon inhalation by the user, it is possible to add a sufficient flavor to the air passing through the flavor generating source 2.

According to the non-burning type flavor inhaler 1 of the second embodiment, as compared to the case when the inlet portion 9 is provided only in the side surface 23, it is possible to shorten the length of the flow path inside the flavor generating source 2. Accordingly, it is possible to control a rise in the air-flow resistance.

(5) Configuration of the Non-Burning Type Flavor Inhaler According to a First Modification Hereinafter, a first modification of the second embodiment will be described. Mainly, the differences from the second embodiment are explained below. The same symbols have been used for the configuration the same as the second embodiment, and the explanation has been omitted.

In the second embodiment, the heat source is laminated on one of the main surfaces of the flavor generating source. In contrast, in the first modification, the heat source is laminated on both of the pair of main surfaces of the flavor generating source.

Figure 12:
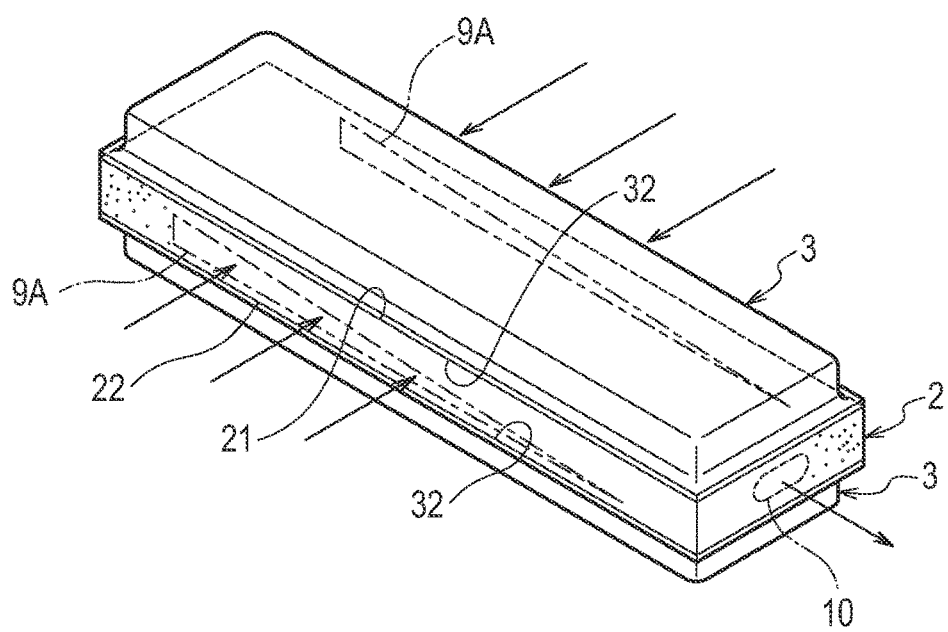
FIG. 12 is a drawing showing a flow path of air in a case when the flavor generating source 2 and two heat sources 3 are inserted in the non-burning type flavor inhaler 2 according to a modification 1 of the second embodiment.

FIG. 12 is a drawing showing a flow path of air in the flavor generating source 2 and the heat source 3, in a case when the flavor generating source 2 and two heat sources 3 are inserted in the holder 4 of the non-burning type flavor inhaler 1.

As shown in FIG. 12, the flavor generating source 2 and the heat source 3 are laminated inside the holder 4 so that one main surface 32 of the heat source 3 and one main surface 21 of the flavor generating source 2 are facing each other, and the main surface 32 of the other heat source 3 and the other main surface 22 of the flavor generating source 2 are facing each other. Therefore, the entire surface of the both main surfaces 21 and 22 of the flavor generating source 2 are heated via the entire surface of the main surface 32 of the two heat sources 3.

According to the non-burning type flavor inhaler 1 of the first modification, since both the main surfaces 21 and 22 of the flavor generating source 2 are heated via the main surface 32 of the two heat sources 3, it is possible to sufficiently heat the flavor generating source 2. It is possible to sufficiently heat the flavor generating source 2, and thus, upon inhalation by the user, it is possible to add a sufficient flavor to the air passing through the flavor generating source 2.

Third Embodiment

Hereinafter, a third embodiment will be described. Mainly, the differences from the second embodiment are explained below. The same symbols have been used for the configuration the same as the second embodiment, and the explanation has been omitted.

(1) Configuration of Non-Burning Type Flavor Inhaler

In the second embodiment, since the inlet openings are formed in both the wall panels rising up from near the longitudinal direction of the bottom panel of the holder, the inlet portions of air into the flavor generating source are provided on both the side surfaces of the flavor generating source facing the inlet opening. Moreover, in the second embodiment, the width of the flavor generating source and the heat source in the lateral direction, and the width of the holder are almost the same.

In contrast, in the third embodiment, since the inlet opening is formed in one of the wall panels rising up from near the longitudinal direction of the bottom panel of the holder, the inlet portion of air into the flavor generating source is provided on one of the side surfaces of the flavor generating source that are facing the inlet opening. Moreover, in the third embodiment, since the width of the flavor generating source and the heat source in the lateral direction is lesser than the width of the holder, a space is formed inside the holder. In addition, the mouthpiece is formed to lead to the space of the holder.

Figure 13:
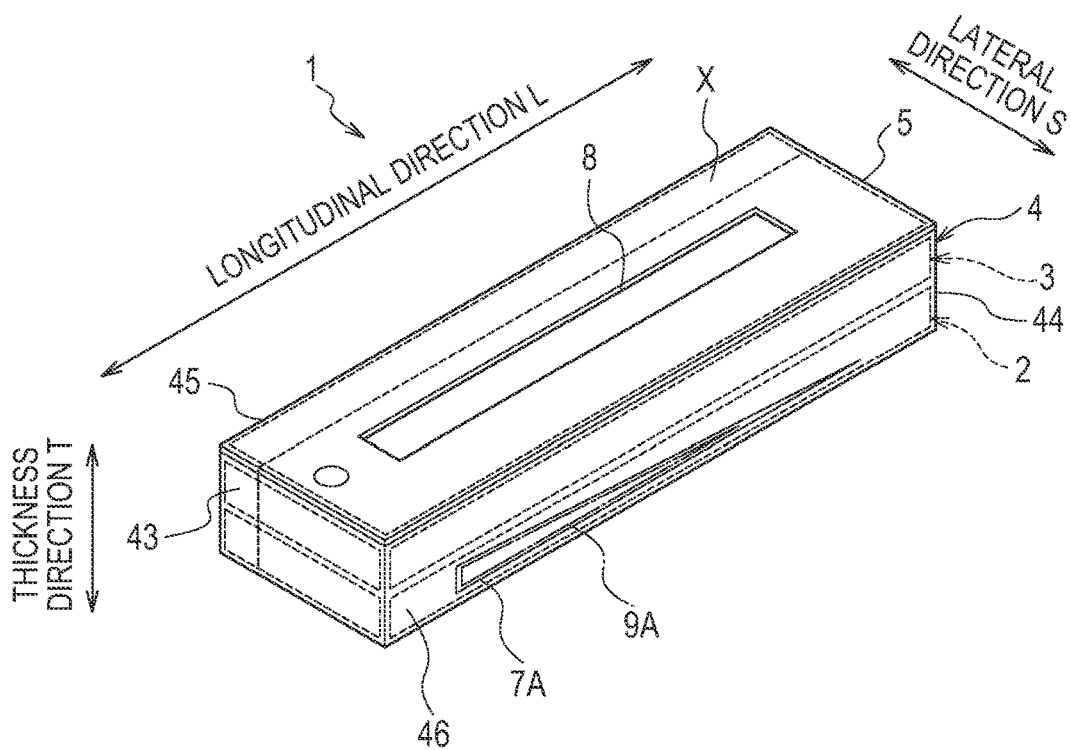
FIG. 13 is a perspective view of the non-burning type flavor inhaler 1 according to a third embodiment.
Figure 14:
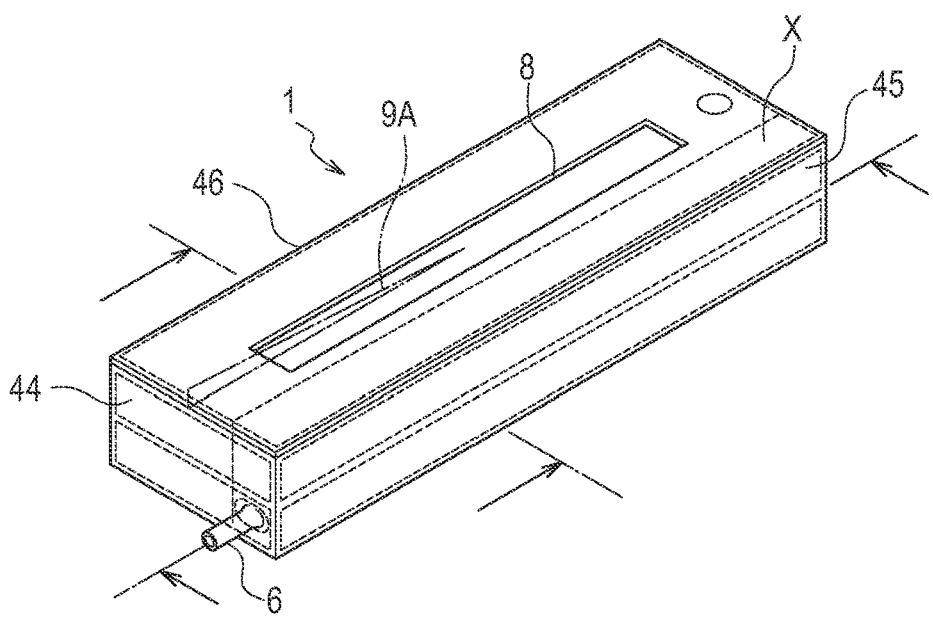
FIG. 14 is a perspective view of the non-burning type flavor inhaler 1 according to the third embodiment.
Figure 15:
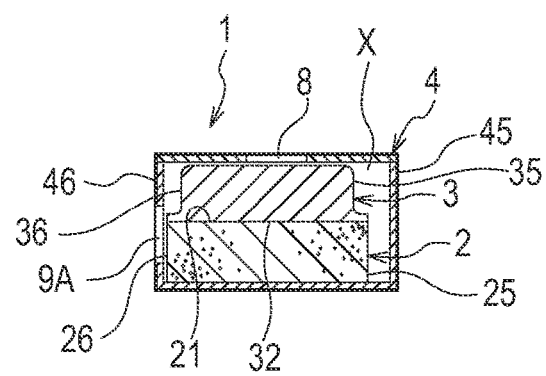
FIG. 15 is a cross-sectional view along a lateral direction of the non-burning type flavor inhaler 1 according to the third embodiment.
Figure 16:
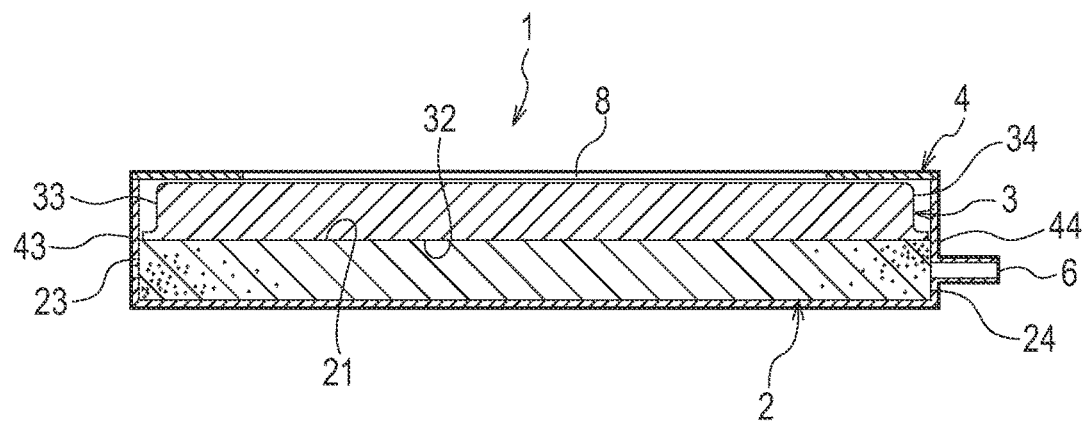
FIG. 16 is a cross-sectional view along a longitudinal direction of the non-burning type flavor inhaler 1 according to the third embodiment.

FIG. 13 and FIG. 14 are perspective views of the non-burning type flavor inhaler 1 according to the third embodiment. FIG. 15 is a cross-sectional view along the lateral direction of the non-burning type flavor inhaler 1 according to the third embodiment. FIG. 16 is a cross-sectional view along the longitudinal direction L of the non-burning type flavor inhaler 1 according to the third embodiment.

As shown in FIG. 13 and FIG. 14, the inlet opening 7A is an opening that leads in air, and is formed only on the wall panel 46 of the holder 4. The inlet opening 7A is not formed in the wall panel 45 of the holder 4.

The mouthpiece 6 is formed in the wall panel 44 along the lateral direction S, in the proximity of the wall panel 45.

As shown in FIG. 15, the side surface 25 of the flavor generating source 2 and the side surface 35 of the heat source 3, as well as the wall panel 45 of the holder 4 do not lie in proximity. A space X is formed between the side surface 25 of the flavor generating source 2 and the side surface 35 of the heat source 3, as well as the wall panel 45 of the holder 4. That is, the width of the flavor generating source and the heat source in the lateral direction S is lesser than the width of the holder. The mouthpiece 6 is formed to lead to the space X of the holder 4.

As shown in FIG. 16, the side surface 23 of the flavor generating source 2 and the side surface 33 of the heat source 3, as well as the wall panel 43 of the holder 4 lie in proximity. The side surface 24 of the flavor generating source 2 and the side surface 34 of the heat source 3, as well as the wall panel 44 of the holder 4 lie in proximity. That is, the length of the flavor generating source 2 and the heat source 3 in the longitudinal direction L, and the length of the holder 4 are almost the same.

(2) Inlet Portion and Outlet Portion

Figure 17:
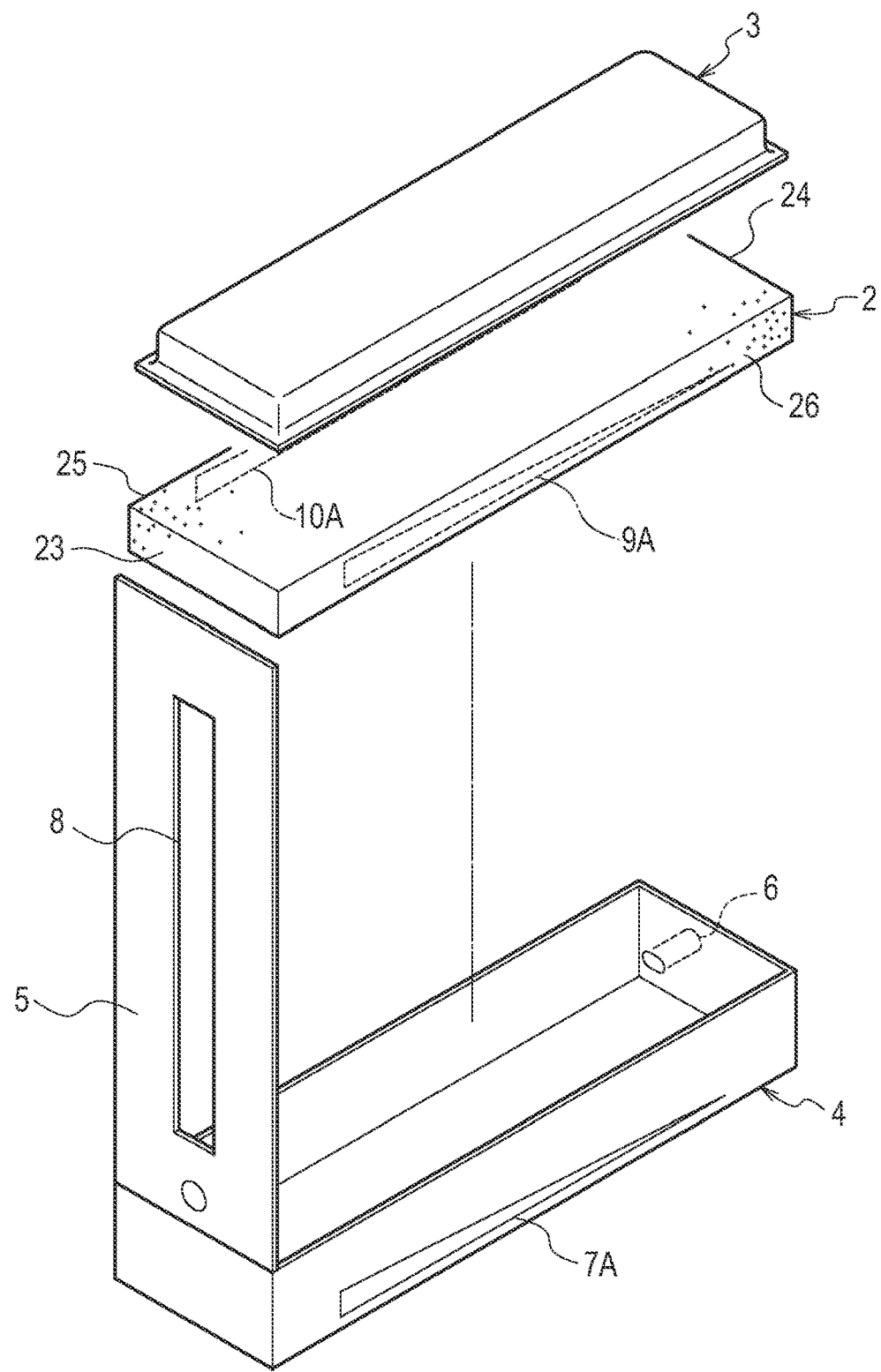
FIG. 17 is a perspective view of the non-burning type flavor inhaler 1 having the open lid 5 according to the third embodiment.

Next, the inlet portion 9A and the outlet portion 10A of the flavor generating source 2 will be described on the basis of FIG. 17. FIG. 17 is a perspective view of the non-burning type flavor inhaler 1 having the open lid 5 according to the third embodiment.

The inlet portion 9A is the portion where the air flowing in from the inlet opening 7A of the holder 4 is led in to the flavor generating source 2, and this area faces the inlet opening 7A provided only on the wall panel 46 of the holder 4. The outlet portion 10A is the portion where the air that has passed through the inside of the flavor generating source 2 is led out, and the outlet portion 10A faces the wall panel 45 of the holder 4. That is, the inlet portion 9A and the outlet portion 10A are provided on the surfaces other than the main surface facing the heat source 3, among the surfaces provided in the flavor generating source 2.

As shown in FIG. 17, the inlet portion 9A of the flavor generating source 2 faces the inlet opening 7A of the holder 4. To enable approximately the same amount of air to be led in throughout the longitudinal direction L in the inlet portion 9A of the flavor generating source 2, the inlet opening 7A of the holder 4 is formed so as to narrow down gradually from the wall panel 43 that does not have the mouthpiece 6 toward the wall panel 44 that has the mouthpiece 6. Therefore, approximately the same amount of air is led out throughout the longitudinal direction L in the outlet portion 10A of the flavor generating source 2 as well.

(3) Flow Path of Air in the Non-Burning Type Flavor Inhaler

Figure 18:
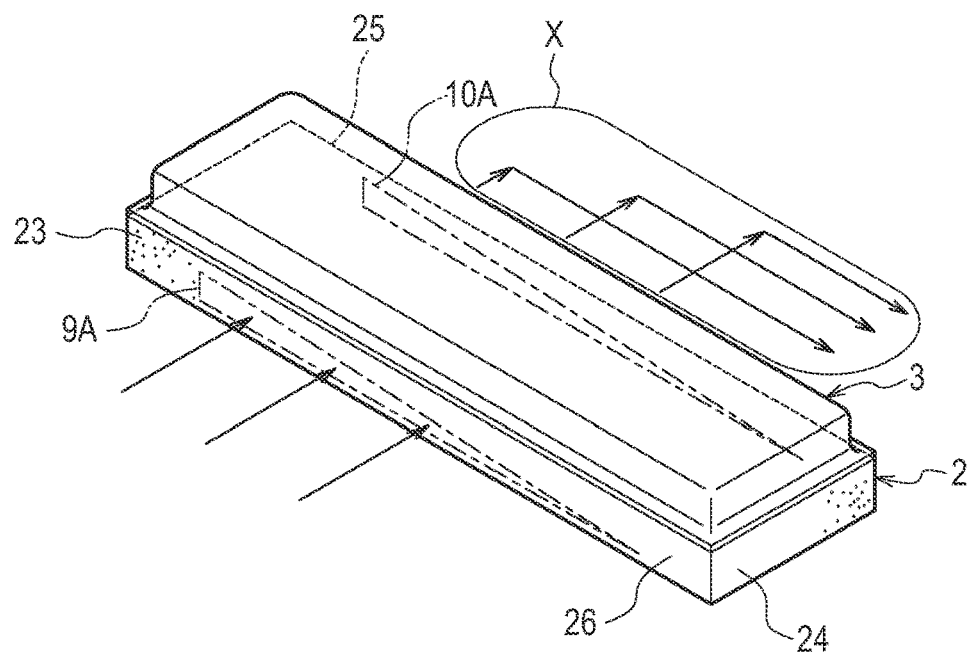
FIG. 18 is a drawing showing a flow path of air in a case when the flavor generating source 2 and the heat source 3 are inserted in the non-burning type flavor inhaler 1 according to the third embodiment.

Next, the flow path of air in the non-burning type flavor inhaler 1 will be described on the basis of FIG. 18. FIG. 18 is a drawing showing a flow path of air in the flavor generating source 2 and the heat source 3, in a case when the flavor generating source 2 and the heat source 3 are inserted in the holder 4 of the non-burning type flavor inhaler 1.

As shown in FIG. 18, upon being inhaled by the user, the air led in from only the inlet portion 9A of the flavor generating source 2 via the inlet opening 7A of the holder 4 passes through the outlet portion 10A of the flavor generating source 2, and is then led out from the mouthpiece 6. As the area of the inlet opening 7A keeps widening further away from the mouthpiece 6, approximately the same amount of air is led into the flavor generating source 2 in the inlet portion 9A close to the side surface 24 and the inlet portion 9A close to the side surface 23.

Since the main surface 32 of the heat source 3 facing the main surface 21 of the flavor generating source 2 does not have air permeability, the air led in from the inlet portion 9A of the flavor generating source 2 is led out from the outlet portion 10A of the flavor generating source 2 without passing through the inside of the heat source 3. That is, the air led in to the inlet portion 9A parallel to the lateral direction and led out from the outlet portion 10A is led out from the mouthpiece 6 after changing the direction in the space X of the holder 4 so as to become parallel to the longitudinal direction L. That is, the holder 4 that stores the flavor generating source 2 and the heat source 3 has a flow path in which the air led in along the lateral direction S is led out from the mouthpiece 6 after changing the direction in the space X so as to become parallel to the longitudinal direction L.

(4) Effect

According to the non-burning type flavor inhaler 1 of the third embodiment, the air that passes through inside the flavor generating source 2 passes through approximately parallel to the lateral direction S, it is possible to shorten the length of the flow path, and possible to control the rise in the air-flow resistance.

(5) Configuration of the Non-Burning Type Flavor Inhaler According to a First Modification Hereinafter, a first modification of the third embodiment will be described. Mainly, the differences from the third embodiment are explained below. The same symbols have been used for the configuration the same as the third embodiment, and the explanation has been omitted.

In the third embodiment, the heat source is laminated on one of the main surfaces of the flavor generating source. In contrast, in the first modification, the heat source is laminated on both of the pair of main surfaces of the flavor generating source.

Figure 19:
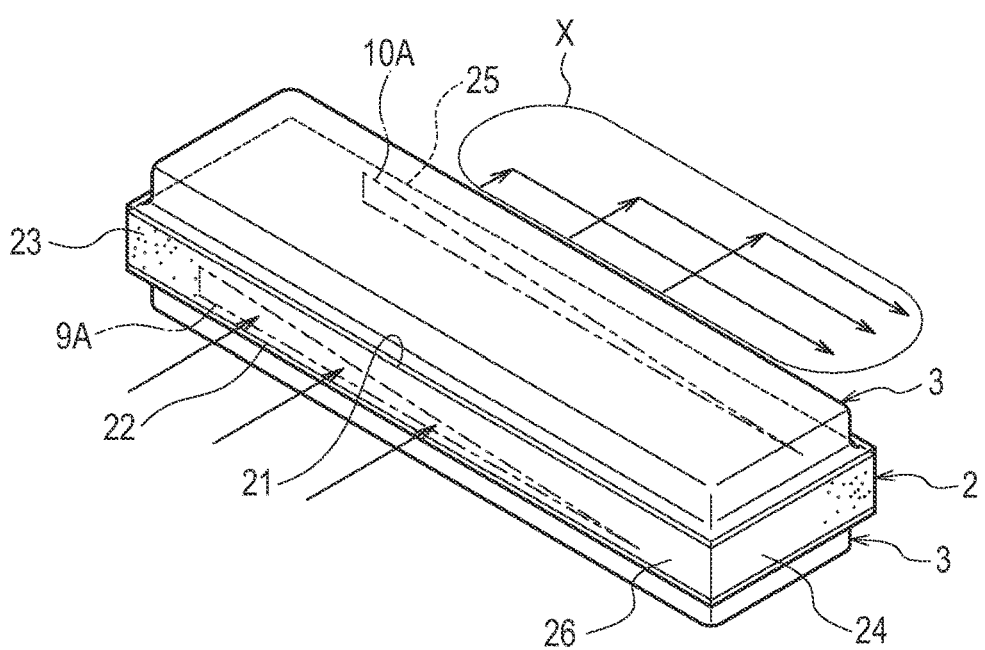
FIG. 19 is a drawing showing a flow path of air in a case when the flavor generating source 2 and two heat sources 3 are inserted in the non-burning type flavor inhaler 3 according to a modification 1 of the third embodiment.

FIG. 19 is a drawing showing a flow path of air in a case when the flavor generating source 2 and two heat sources 3 are inserted in the non-burning type flavor inhaler 1.

As shown in FIG. 19, the flavor generating source 2 and the heat source 3 are laminated inside the holder 4 so that one main surface 32 of the heat source 3 and one main surface 21 of the flavor generating source 2 are facing each other, and the main surface 32 of the other heat source 3 and the other main surface 22 of the flavor generating source 2 are facing each other. Therefore, the entire surface of the both main surfaces 21 and 22 of the flavor generating source 2 are heated via the entire surface of the main surface 32 of the two heat sources 3.

According to the non-burning type flavor inhaler 1 of the first modification, since both the main surfaces 21 and 22 of the flavor generating source 2 are heated via the main surface 32 of the two heat sources 3, it is possible to sufficiently heat the flavor generating source 2. It is possible to sufficiently heat the flavor generating source 2, and thus, upon inhalation by the user, it is possible to add a sufficient flavor to the air passing through the flavor generating source 2.

Fourth Embodiment

Hereinafter, a fourth embodiment will be described. Mainly, the differences from the second embodiment are explained below. The same symbols have been used for the configuration the same as the second embodiment, and the explanation has been omitted.

(1) Configuration of Non-Burning Type Flavor Inhaler

In the second embodiment, in both the wall panels rising from near the longitudinal direction of the bottom panel of the holder, the inlet opening is formed so that the area of the inlet opening reduces gradually from the wall panel that does not have the mouthpiece toward the wall panel that has the mouthpiece.

In contrast, in the fourth embodiment, the inlet opening formed in both the wall panels rising from near the longitudinal direction of the bottom panel of the holder is approximately the same shape across the longitudinal direction.

In the second embodiment, the non-burning type flavor inhaler has a holder that stores a flavor generating source and a heat source.

In contrast, in the fourth embodiment, the non-burning type flavor inhaler has a holder that stores a flavor generating source, a heat source, and a rectification member.

Figure 20:
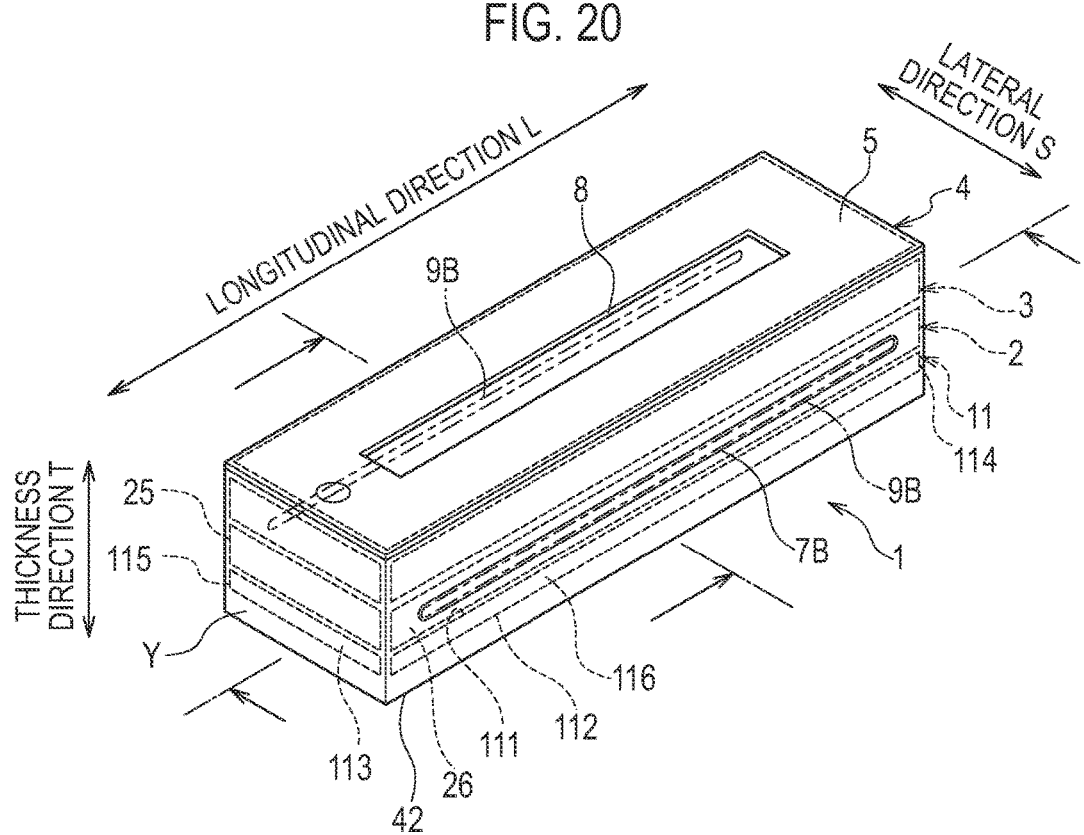
FIG. 20 is a perspective view of the non-burning type flavor inhaler 1 according to a fourth embodiment.
Figure 21:
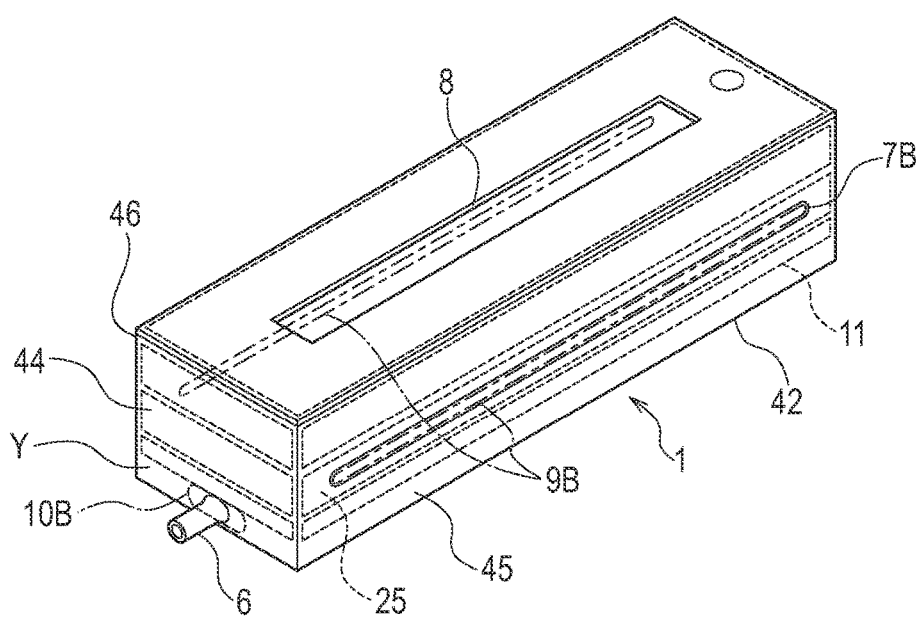
FIG. 21 is a perspective view of the non-burning type flavor inhaler 1 according to the fourth embodiment.
Figure 22:
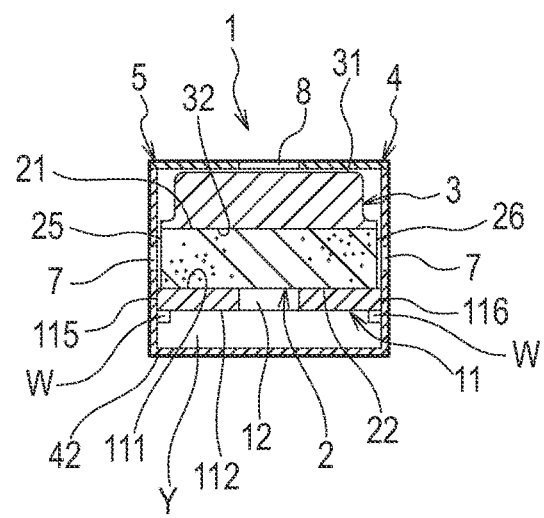
FIG. 22 is a cross-sectional view along a lateral direction of the non-burning type flavor inhaler 1 according to the fourth embodiment.
Figure 23:
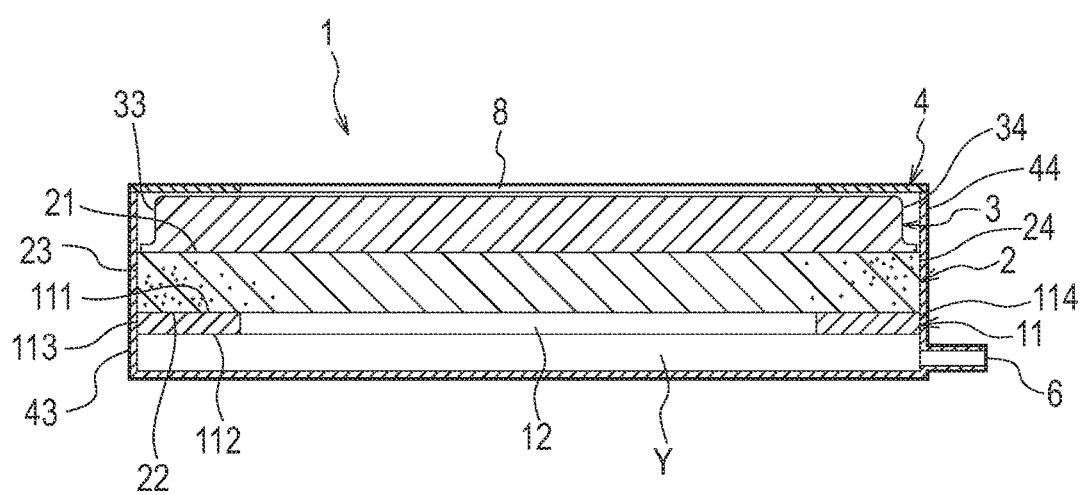
FIG. 23 is a cross-sectional view along a longitudinal direction of the non-burning type flavor inhaler 1 according to the fourth embodiment.

FIG. 20 and FIG. 21 are perspective views of the non-burning type flavor inhaler 1 according to the fourth embodiment. FIG. 22 is a cross-sectional view along a lateral direction of the non-burning type flavor inhaler 1 according to the fourth embodiment. FIG. 23 is a cross-sectional view along the longitudinal direction L of the non-burning type flavor inhaler 1 according to the fourth embodiment.

The non-burning type flavor inhaler 1 includes a flavor generating source 2, a heat source 3, a holder 4, a lid 5, a mouthpiece 6, and a rectification member 11.

As shown in FIG. 20 and FIG. 21, the inlet opening 7B is an opening that leads in air, and is formed on both the wall panels 45 and 46 of the holder 4. The inlet opening 7B may be line-shaped. Moreover, the inlet opening 7B may be dot-shaped. A dot shape is a shape in which a plurality of small openings are collected together.

As shown in FIG. 20 and FIG. 21, both the side surfaces 25 and 26 of the flavor generating source 2 have an inlet portion 9B. The main surface 22 of the flavor generating source 2 has an outlet portion 10B. The inlet portion 9B and the outlet portion 10B will be described in detail later.

As shown in FIG. 20 and FIG. 21, the mouthpiece 6 leads to the inner side of the holder 4, and has a cylindrical shape. The mouthpiece 6 is formed in a circular shape in the center of the wall panel 44 of the holder 4. The center of the wall panel 44 of the holder 4 is provided at a position whose distance from the pair of wall panels 45 and 46 along the longitudinal direction L is approximately equal.

As shown in FIGS. 20 and 21, the rectification member 11 has the widest area and a plate shape (an approximately rectangular parallelepiped shape) including a pair of main surfaces 111 and 112 defined by the longitudinal direction L and the lateral direction S, a pair of side surfaces 113 and 114 defined by the lateral direction S and the thickness direction T, and a pair of side surfaces 115 and 116 defined by the longitudinal direction L and the thickness direction T. A rectification member opening 12 is formed so as to penetrate the pair of main surfaces 111 and 112 provided in the rectification member 11.

As shown in FIG. 22, the flavor generating source 2 and the heat source 3 are laminated inside the holder 4 so that the main surface 32 of the heat source 3 and the main surface 21 of the flavor generating source 2 are facing each other. The flavor generating source 2 and the rectification member 11 are laminated inside the holder 4 so that the main surface 22 of the flavor generating source 2 and the main surface 111 of the rectification member are facing each other. The main surface 31 of the heat source 3 and the lid 5 lie in proximity, and are stored in the holder 4 so that the air is supplied from the main surface 31 of the heat source 3 via the opening 8 of the lid 5. Inside the holder 4, the rectification member 11 is installed on a convex portion W protruding in the inner side along the lateral direction S along the longitudinal direction L. In other words, the rectification member 11 is stored inside the holder 4 so that a space Y is formed between the main surface 112 of the rectification member 11 and the bottom panel 42 of the holder 4. That is, the thickness obtained by laminating the flavor generating source 2, the heat source 3, and the rectification member 11, in the thickness direction T, is lesser than the thickness of the holder 4. Furthermore, the side surface 25 of the flavor generating source 2, the side surface 35 of the heat source 3, and the side surface 115 of the rectification member 11, as well as the wall panel 45 of the holder 4 lie in proximity. The side surface 26 of the flavor generating source 2, the side surface 36 of the heat source 3, and the side surface 116 of the rectification member 11, as well as the wall panel 46 of the holder 4 lie in proximity. That is, the width of the flavor generating source 2, the heat source 3, and the rectification member 11 in the lateral direction S, and the width of the holder 4 are almost the same.

As shown in FIG. 23, the side surface 23 of the flavor generating source 2, the side surface 33 of the heat source 3, and the side surface 113 of the rectification member 11, as well as the wall panel 43 of the holder 4 lie in proximity. The side surface 24 of the flavor generating source 2, the side surface 34 of the heat source 3, and the side surface 114 of the rectification member 11, as well as the wall panel 44 of the holder 4 lie in proximity. That is, the length of the flavor generating source 2, the heat source 3, and the rectification member 11 in the longitudinal direction L, and the length of the holder 4 are almost the same. The flavor generating source 2, the heat source 3, and the rectification member 11 are stored in the holder 4 so that the space Y and the mouthpiece 6 are facing each other.

(2) Inlet Portion and Outlet Portion

Figure 24:
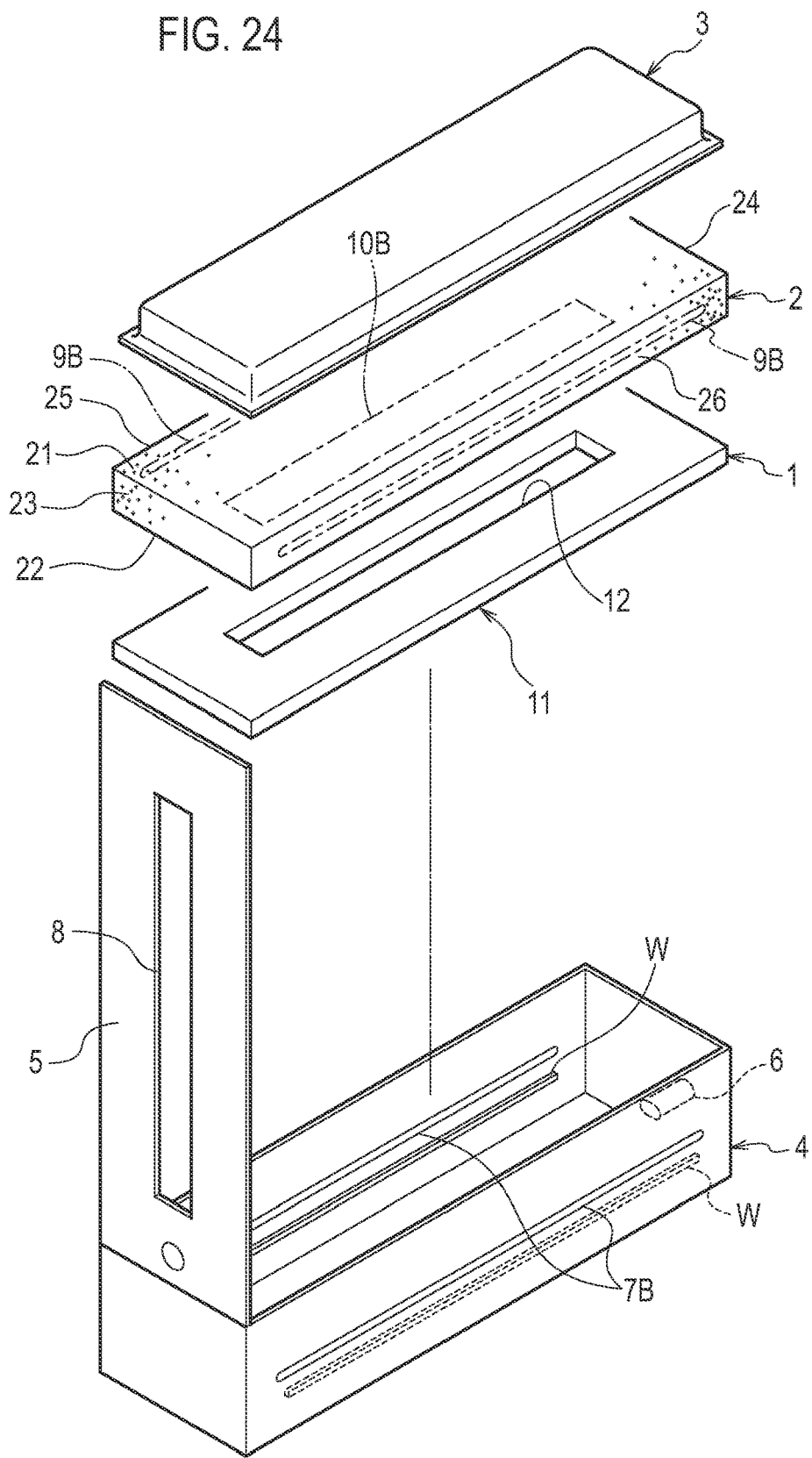
FIG. 24 is a perspective view of the non-burning type flavor inhaler 1 having the open lid 5 according to the fourth embodiment.

Next, the inlet portion 9B and the outlet portion 10B of the flavor generating source 2 will be described on the basis of FIG. 24. FIG. 24 is a perspective view of the non-burning type flavor inhaler 1 having the open lid 5 according to the fourth embodiment.

The inlet portion 9B is the portion where the air flowing in from the inlet opening 7B is led in to the inside of the flavor generating source 2, and this area faces each inlet opening 7B provided on the wall panels of the holder 4. The outlet portion 10B is the portion where the air that has passed through the inside of the flavor generating source 2 is led out, and the outlet portion 10B faces the space Y via the rectification member 11. That is, the inlet portion 9B is provided on the surface other than the main surface facing the heat source 3, among the surfaces provided in the flavor generating source 2.

(3) Flow Path of Air in the Non-Burning Type Flavor Inhaler

Figure 25:
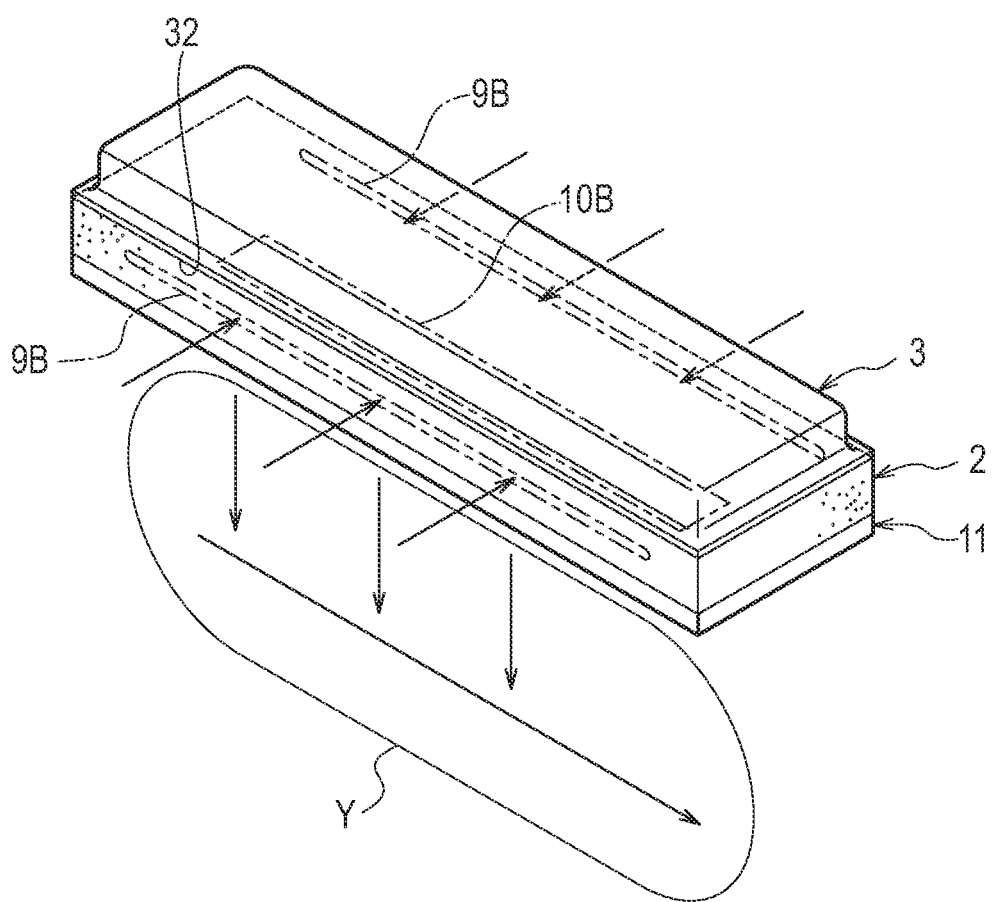
FIG. 25 is a drawing showing a flow path of air in a case when the flavor generating source 2 and the heat source 3 are inserted in the non-burning type flavor inhaler 1 according to the fourth embodiment.

Next, the flow path of air in the non-burning type flavor inhaler 1 will be described on the basis of FIG. 25. FIG. 25 is a drawing showing a flow path of air in a case when the flavor generating source 2 and the heat source 3 is inserted in the non-burning type flavor inhaler 1.

As shown in FIG. 25, upon being inhaled by the user, the air led in from the inlet portion 9B of the flavor generating source 2 via the inlet opening 7B of the holder 4 passes through the outlet portion 10B of the flavor generating source 2 and the rectification member opening 12 of the rectification member 11, and is then led out from the mouthpiece 6. Since the main surface 32 of the heat source 3 that is facing the flavor generating source 2 does not have air permeability, the air led in from the inlet portion 9B of the flavor generating source 2 is led out from the outlet portion 10B of the flavor generating source 2 without passing through the inside of the heat source 3. That is, the air led in to the inlet portion 9B parallel to the lateral direction S and led out from the outlet portion 10B is led out from the mouthpiece 6 after changing the direction in the flavor generating source 2 so as to become perpendicular to the lateral direction S and the longitudinal direction L, and then again changing the direction in the space Y of the holder 4 so as to become parallel to the longitudinal direction L. That is, the holder 4 that stores the flavor generating source 2 and the heat source 3 has a flow path where the air led in to the inlet portion 9B parallel to the lateral direction S and led out from the outlet portion 10B is led out from the mouthpiece after changing the direction in the flavor generating source 2 so as to become perpendicular to the lateral direction S and the longitudinal direction L, then passing through the rectification member opening 12, and then again changing the direction in the space Y of the holder 4 so as to become parallel to the longitudinal direction L. By controlling the air led out from the outlet portion 10B, the rectification member 11 leads the air into the space Y of the holder 4.

(4) Effect

According to the non-burning type flavor inhaler 1 of the fourth embodiment, the flow of the air led in to the inlet portion 9B parallel to the lateral direction S and led out from the outlet portion 10B is controlled by the rectification member 11 so that the air flows through the entire inside of the flavor generating source 2, and as a result, upon being inhaled by the user, it is possible to control the air-flow resistance while adding sufficient flavor to the air passing through the flavor generating source 2.

Fifth Embodiment

Hereinafter, a fifth embodiment will be described. Mainly, the differences from the fourth embodiment are explained below. The same symbols have been used for the configuration the same as the fourth embodiment, and the explanation has been omitted.

(1) Configuration of Non-Burning Type Flavor Inhaler

In the fourth embodiment, the thickness obtained by laminating the flavor generating source, the heat source, and the rectification member, in the thickness direction T, is lesser than the thickness of the holder. Furthermore, in the fourth embodiment, the mouthpiece is formed in one of the wall panels rising up from near the lateral direction of the bottom panel of the holder.

In contrast, in the fifth embodiment, the thickness obtained by laminating the flavor generating source, the heat source, and the rectification member, in the thickness direction, is almost same as the thickness of the holder. In addition, in the fifth embodiment, the mouthpiece is formed in the bottom panel of the holder.

Figure 26:
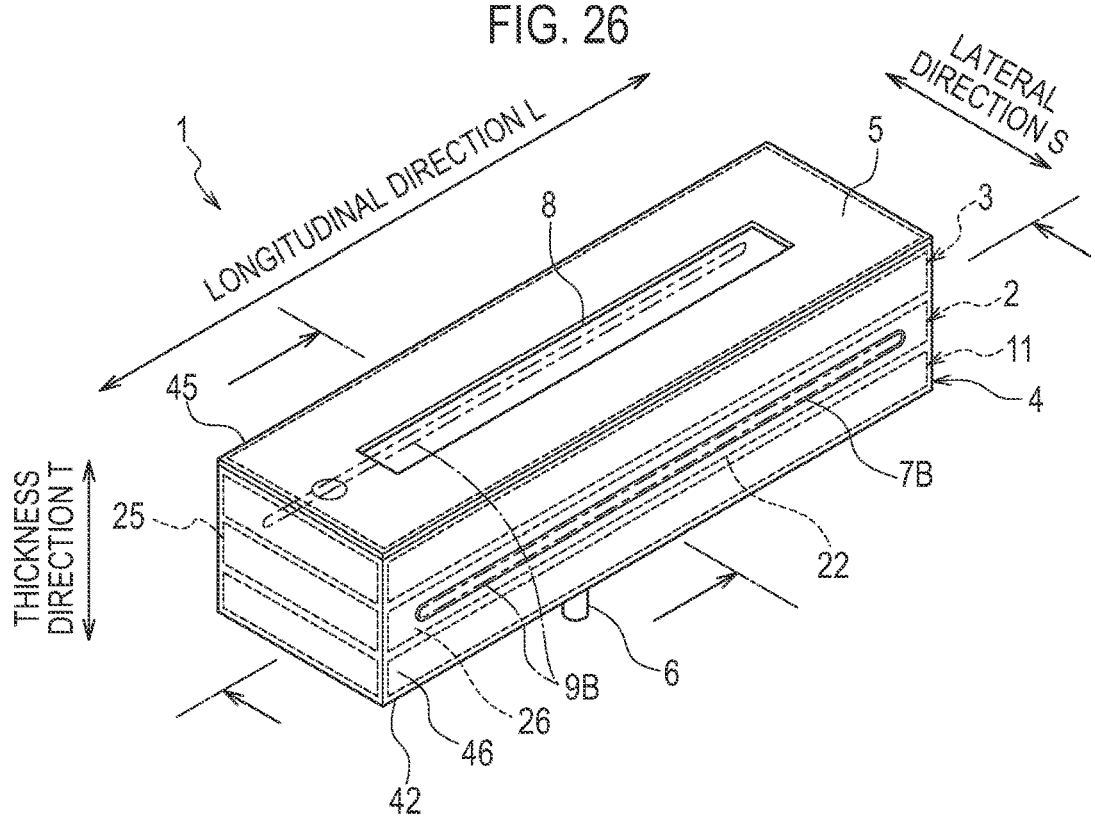
FIG. 26 is a perspective view of the non-burning type flavor inhaler 1 according to a fifth embodiment.
Figure 27:
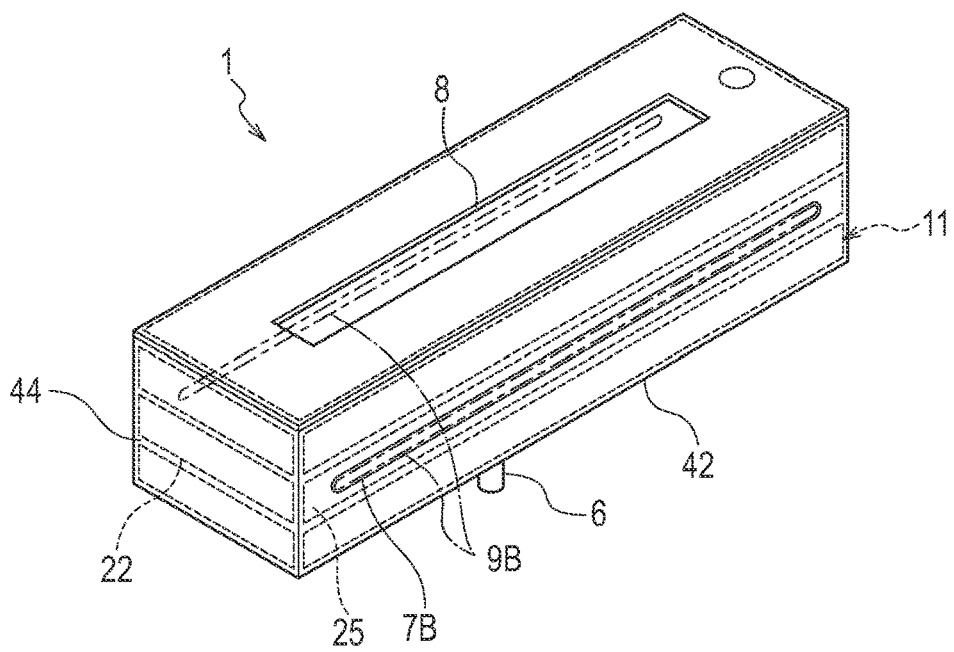
FIG. 27 is a perspective view of the non-burning type flavor inhaler 1 according to the fifth embodiment.
Figure 28:
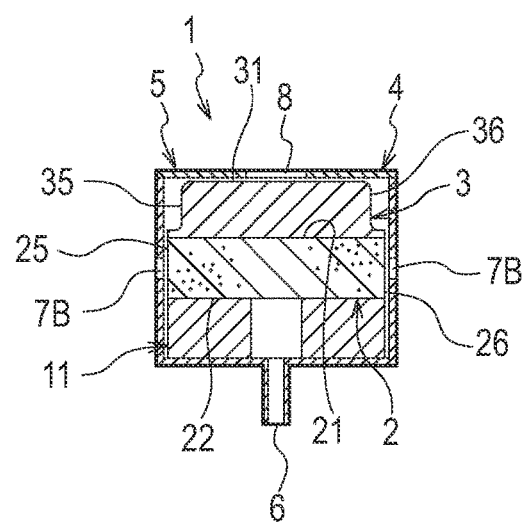
FIG. 28 is a cross-sectional view along a lateral direction of the non-burning type flavor inhaler 1 according to the fifth embodiment.
Figure 29:
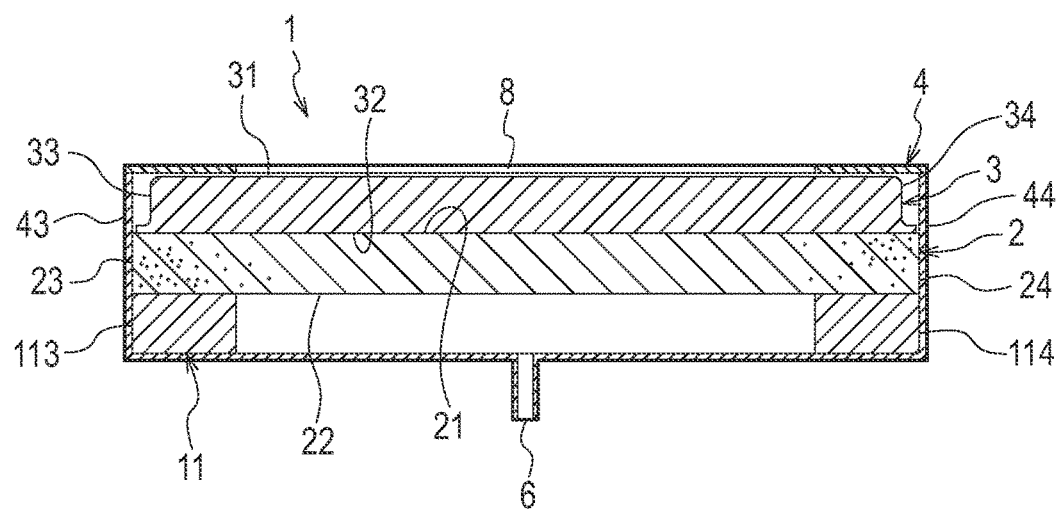
FIG. 29 is a cross-sectional view along a longitudinal direction of the non-burning type flavor inhaler 1 according to the fifth embodiment.

Next, the configuration of the non-burning type flavor inhaler 1 according to the fifth embodiment will be described on the basis of FIG. 26 through FIG. 29. FIG. 26 and FIG. 27 are perspective views of the non-burning type flavor inhaler 1 according to the fifth embodiment. FIG. 28 is a cross-sectional view along the lateral direction of the non-burning type flavor inhaler 1 according to the fifth embodiment. FIG. 29 is a cross-sectional view along the longitudinal direction L of the non-burning type flavor inhaler 1 according to the fifth embodiment.

As shown in FIG. 26 and FIG. 27, both the side surfaces 25 and 26 of the flavor generating source 2 have an inlet portion 9B. The main surface 22 of the flavor generating source 2 has an outlet portion 10B. The inlet portion 9B and the outlet portion 10B will be described in detail later.

The mouthpiece 6 leads to the inner side of the holder 4, and has a cylindrical shape. The mouthpiece 6 is formed in a circular shape in the center of the bottom panel 42 of the holder 4. The center of the bottom panel 42 of the holder 4 is provided at a position whose distance from the pair of wall panels 45 and 46 along the longitudinal direction L, and the pair of wall panels 43 and 44 along the lateral direction S is approximately equal.

As shown in FIG. 28, the flavor generating source 2 and the heat source 3 are laminated inside the holder 4 so that the main surface 32 of the heat source 3 and the main surface 21 of the flavor generating source 2 are facing each other. The flavor generating source 2 and the rectification member 11 are laminated inside the holder 4 so that the main surface 22 of the flavor generating source 2 and the main surface 111 of the rectification member 11 are facing each other. The main surface 31 of the heat source 3 and the lid 5 lie in proximity, and are stored in the holder 4 so that the air is supplied from the main surface 31 of the heat source 3 via the opening 8 of the lid 5. The rectification member 11 is stored inside the holder 4 so that the main surface 112 of the rectification member 11 and the bottom panel 42 of the holder 4 are in close contact. That is, the thickness obtained by laminating the flavor generating source 2, the heat source 3, and the rectification member 11, in the thickness direction T, is almost same as the thickness of the holder 4. Furthermore, the side surface 25 of the flavor generating source 2, the side surface 35 of the heat source 3, and the side surface 115 of the rectification member 11, as well as the wall panel 45 of the holder 4 lie in proximity. The side surface 26 of the flavor generating source 2, the side surface 36 of the heat source 3, and the side surface 116 of the rectification member 11, as well as the wall panel 46 of the holder 4 lie in proximity. That is, the width of the flavor generating source 2, the heat source 3, and the rectification member 11 in the lateral direction S, and the width of the holder 4 are almost the same.

As shown in FIG. 29, the side surface 23 of the flavor generating source 2, the side surface 33 of the heat source 3, and the side surface 113 of the rectification member 11, as well as the wall panel 43 of the holder 4 lie in proximity. The side surface 24 of the flavor generating source 2, the side surface 34 of the heat source 3, and the side surface 114 of the rectification member 11, as well as the wall panel 44 of the holder 4 lie in proximity. That is, the length of the flavor generating source 2, the heat source 3, and the rectification member 11 in the longitudinal direction L, and the length of the holder 4 are almost the same. The rectification member 11 is stored in the holder 4 so that the rectification member opening 12 of the rectification member 11 faces the mouthpiece 6.

(2) Inlet Portion and Outlet Portion

Figure 30:
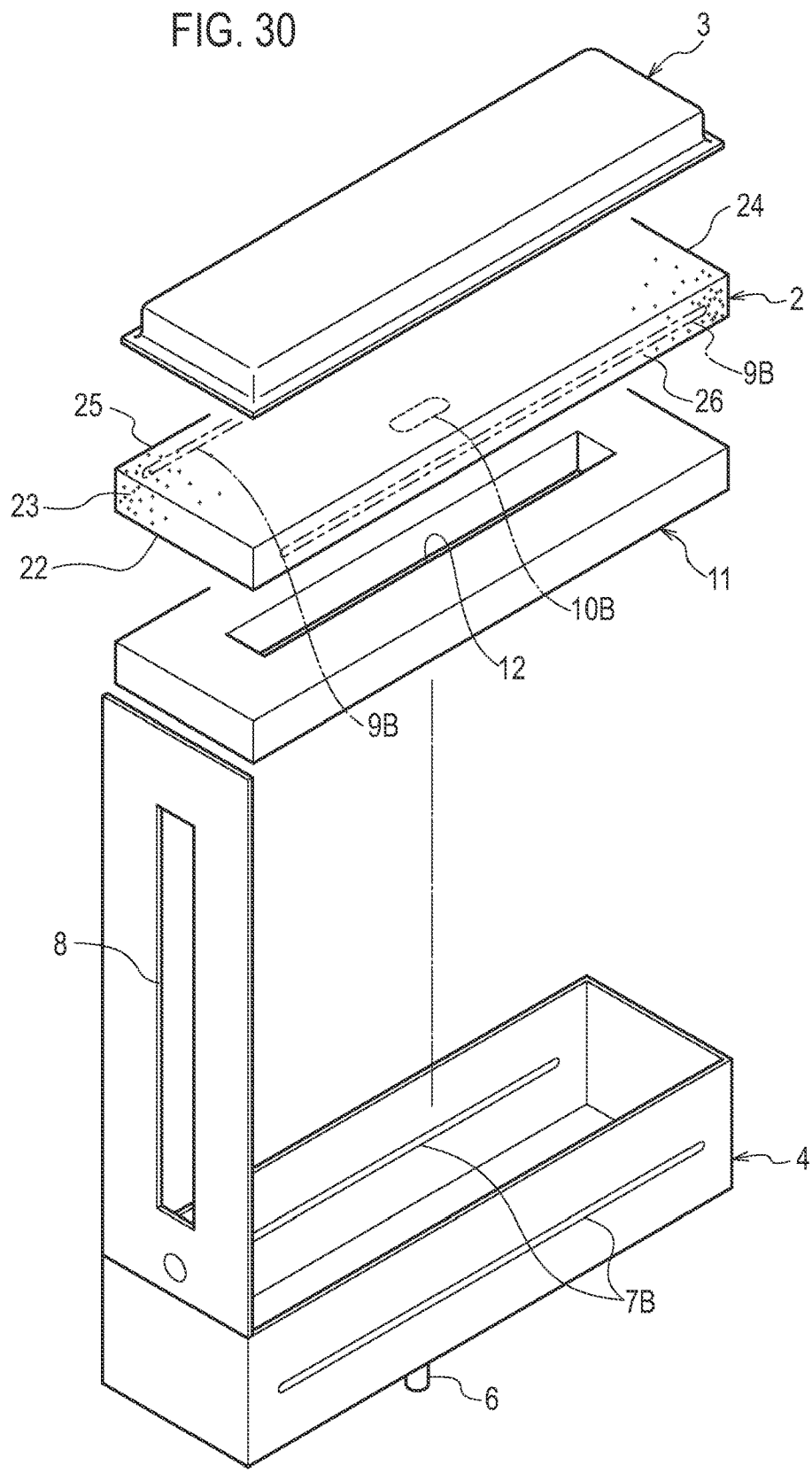
FIG. 30 is a perspective view of the non-burning type flavor inhaler 1 having the open lid 5 according to the fifth embodiment.

Next, the inlet portion 9B and the outlet portion 10B of the flavor generating source 2 will be described on the basis of FIG. 30. FIG. 30 is a perspective view of the non-burning type flavor inhaler 1 having the open lid 5 according to the fifth embodiment.

The inlet portion 9B is the portion where the air flowing in from the inlet opening 7B is led in to the inside of the flavor generating source 2, and this area faces each inlet opening 7B provided on both the wall panels 45 and 46 of the holder 4. The outlet portion 10B is the portion where the air that has passed through the inside of the flavor generating source 2 is led out, and the outlet portion 10B faces the mouthpiece 6. That is, the inlet portion 9B is provided on the surface other than the main surface facing the heat source 3, among the surfaces provided in the flavor generating source 2.

(3) Flow Path of Air in the Non-Burning Type Flavor Inhaler

Figure 31:
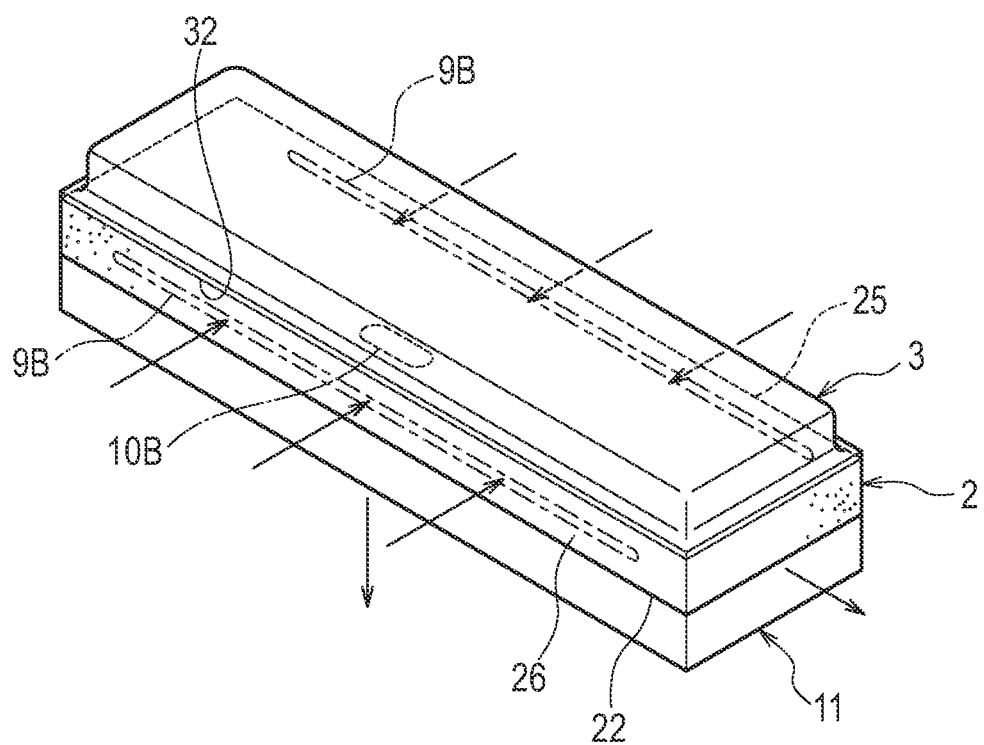
FIG. 31 is a drawing showing a flow path of air in a case when the flavor generating source 2 and the heat source 3 are inserted in the non-burning type flavor inhaler 1 according to the fifth embodiment.

Next, the flow path of air in the non-burning type flavor inhaler 1 will be described on the basis of FIG. 31. FIG. 31 is a drawing showing a flow path of air in the flavor generating source 2 and the heat source 3, in a case when the flavor generating source 2, the heat source 3, and the rectification member 11 are inserted in the holder 4 of the non-burning type flavor inhaler 1.

As shown in FIG. 31, upon being inhaled by the user, the air led in from both the inlet portions 9B of the flavor generating source 2 via the inlet opening 7B of the holder 4 is led out from the outlet portion 10B of the flavor generating source 2. Since the main surface 32 of the heat source 3 that is facing the flavor generating source 2 does not have air permeability, the air led in from the inlet portion 9B of the flavor generating source 2 is led out from the outlet portion 10B of the flavor generating source 2 without passing through the inside of the heat source 3. That is, the air led in to the inlet portion 9B parallel to the lateral direction S and led out from the outlet portion 10b is led out from the mouthpiece 6 after changing the direction in the flavor generating source 2 so as to become perpendicular to the lateral direction S and the longitudinal direction L. That is, the holder 4 that stores the flavor generating source 2 and the heat source 3 has a flow path where the air led in to the inlet portion 9B parallel to the lateral direction S and led out from the outlet portion 10B is led out from the mouthpiece 6 after changing the direction in the flavor generating source 2 so as to become perpendicular to the lateral direction S and the longitudinal direction L.

(4) Effect

According to the non-burning type flavor inhaler 1 of the fifth embodiment, the air led in to the inlet portion 9B parallel to the lateral direction S is led out from the outlet portion 10B after changing the direction in the flavor generating source 2 so as to become perpendicular to the lateral direction S and the longitudinal direction L, and as a result, upon being inhaled by the user, it is possible to control the air-flow resistance while adding sufficient flavor to the air passing through the flavor generating source 2.

In addition, the entire content of Japanese Patent Application No. 2012-231149 (filed on Oct. 18, 2012) is incorporated in the present specification by reference.

INDUSTRIAL APPLICABILITY

According to the characteristics of the present invention, it is possible to provide a non-burning type flavor inhaler having excellent portability and handling, with which it is possible to easily process the shape of the heat source and the flavor generating source.

The invention claimed is:

1. A non-burning type flavor inhaler, comprising:
a heat source having a plate shape including a pair of main surfaces including a first main surface and a second main surface;
a flavor generating source having a plate shape including a pair of main surfaces including a first main surface and a second main surface; and
a holder that stores the heat source and the flavor generating source,
wherein the heat source and the flavor generating source are laminated inside the holder so that the first main surface of the heat source and the first main surface of the flavor generating source are facing each other,
wherein the first main surface of the heat source is laminated to the first main surface of the flavor generating source and the heat source is not laminated on any other surface of the flavor generating source,
wherein the flavor generating source has an inlet portion through which air is led into the flavor generating source, and an outlet portion from which air is led out from the flavor generating source, and wherein the inlet portion and the outlet portion are provided on surfaces other than the main surface facing the heat source, among the surfaces provided in the flavor generating source.

2. The non-burning type flavor inhaler according to claim 1, wherein the pair of main surfaces provided in the flavor generating source have a rectangular shape defined by a lateral direction and a longitudinal direction orthogonal to each other, and wherein the inlet portion is provided on both of a pair of side surfaces along the longitudinal direction, among the surfaces provided in the flavor generating source.

3. The non-burning type flavor inhaler according to claim 2, wherein the outlet portion is provided on the second main surface of the flavor generating source.

4. The non-burning type flavor inhaler according to claim 3, wherein the outlet portion is provided at a position whose distance from the pair of side surfaces along the longitudinal direction is approximately equal.

5. The non-burning type flavor inhaler according to claim 4, wherein the holder has a flow path through which the air led out from the outlet portion is led to a mouthpiece, and wherein the flow path is a space formed along the second main surface of the flavor generating source.

6. The non-burning type flavor inhaler according to claim 2, wherein the outlet portion is provided on any one of a pair of side surfaces along the lateral direction.

7. The non-burning type flavor inhaler according to claim 1, wherein the pair of main surfaces provided in the flavor generating source have a rectangular shape defined by a lateral direction and a longitudinal direction orthogonal to each other, and wherein the inlet portion is provided on a first side surface among a pair of side surfaces provided on opposite sides and the outlet portion is provided on a second other side surface among the pair of side surfaces provided on opposite sides.

8. The non-burning type flavor inhaler according to claim 7, wherein the inlet portion is provided on a first side surface among a pair of side surfaces along the longitudinal direction, wherein the outlet portion is provided on a second side surface among the pair of side surfaces among the pair of side surfaces along the longitudinal direction, wherein the holder has a flow path through which leads the air led out from the outlet portion to the mouthpiece, and wherein the flow path is a space formed along the second side surface.

9. The non-burning type flavor inhaler according to claim 1, wherein the heat source generates heat by a chemical reaction and heats the flavor generating source.

10. The non-burning type flavor inhaler according to claim 9, wherein the chemical reaction is an oxidation reaction of powders.

11. The non-burning type flavor inhaler according to claim 1, wherein the flavor generating source is a compact and includes tobacco powder having air permeability.

12. A non-burning type flavor inhaler, comprising:
a heat source having a plate shape including a pair of main surfaces including a first main surface and a second main surface;
a flavor generating source having a plate shape including a pair of main surfaces including a first main surface and a second main surface; and
a holder that stores the heat source and the flavor generating source,
wherein the heat source and the flavor generating source are laminated inside the holder so that the first main surface of the heat source and the first main surface of the flavor generating source are facing each other,
wherein the flavor generating source has an inlet portion through which air is led into the flavor generating source, and an outlet portion from which air is led out from the flavor generating source,
wherein the inlet portion and the outlet portion are provided on surfaces other than the main surface facing the heat source, among the surfaces provided in the flavor generating source,
wherein the pair of main surfaces provided in the flavor generating source have a rectangular shape defined by a lateral direction and a longitudinal direction orthogonal to each other, and
wherein the inlet portion is provided on both of a pair of side surfaces along the longitudinal direction, among the surfaces provided in the flavor generating source.

13. The non-burning type flavor inhaler according to claim 1, wherein the holder is a rectangular parallelepiped shape.

* * * * *